US010039796B2

(12) United States Patent
Zhang et al.

(10) Patent No.: US 10,039,796 B2
(45) **Date of Patent: *Aug. 7, 2018**

(54) MUTANT HERPES SIMPLEX VIRUS-2 FOR CANCER THERAPY

(71) Applicant: The University of Houston System, Houston, TX (US)

(72) Inventors: Xiaoliu Zhang, Houston, TX (US); Xinping Fu, Houston, TX (US)

(73) Assignee: The University of Houston System, Houston, TX (US)

( * ) Notice: Subject to any disclaimer, the term of this patent is extended or adjusted under 35 U.S.C. 154(b) by 270 days.

This patent is subject to a terminal disclaimer.

(21) Appl. No.: 14/622,263

(22) Filed: Feb. 13, 2015

(65) Prior Publication Data

US 2015/0150920 A1 Jun. 4, 2015

Related U.S. Application Data

(62) Division of application No. 11/922,796, filed as application No. PCT/US2006/024440 on Jun. 23, 2006, now Pat. No. 8,986,672.

(60) Provisional application No. 60/693,157, filed on Jun. 23, 2005.

(51) Int. Cl.

| | |
|---|---|
| ***A61K 35/763*** | (2015.01) |
| ***A61K 39/245*** | (2006.01) |
| ***C07K 14/005*** | (2006.01) |
| ***C12N 7/00*** | (2006.01) |
| ***C12N 15/86*** | (2006.01) |
| ***A61K 38/17*** | (2006.01) |
| *A61K 38/00* | (2006.01) |
| *A61K 39/00* | (2006.01) |

(52) U.S. Cl.

CPC ........ *A61K 35/763* (2013.01); *A61K 38/1709* (2013.01); *A61K 39/245* (2013.01); *C07K 14/005* (2013.01); *C12N 7/00* (2013.01); *C12N 15/86* (2013.01); *A61K 38/00* (2013.01); *A61K 2039/5256* (2013.01); *A61K 2039/572* (2013.01); *A61K 2039/585* (2013.01); *C07K 2319/01* (2013.01); *C12N 2710/16622* (2013.01); *C12N 2710/16632* (2013.01); *C12N 2710/16643* (2013.01); *C12N 2710/16671* (2013.01); *C12N 2810/60* (2013.01)

(58) Field of Classification Search

CPC ....... A61K 35/763; C07K 14/005; C12N 7/00

See application file for complete search history.

(56) References Cited

U.S. PATENT DOCUMENTS

| | | | | |
|---|---|---|---|---|
| 6,013,265 A * | 1/2000 | Aurelian | C07K 14/005 424/199.1 |
| 6,054,131 A | 4/2000 | Aurelian | |
| 2004/0009604 A1 * | 1/2004 | Zhang | A61K 48/0058 435/456 |
| 2012/0301506 A1 | 11/2012 | Zhang | |

FOREIGN PATENT DOCUMENTS

| | | |
|---|---|---|
| EP | 1327688 A | 7/2003 |
| WO | 1999036084 A | 7/1999 |
| WO | 2003073918 | 12/2003 |

OTHER PUBLICATIONS

Smith et al J. Virol.2000, 74: 10417-10429.*

Downward, J.Nat. Rev. 2003, Cancer 3: 11-22.*

Aurelian, et al., "Vaccine potential of a herpes simplex virus type 2 mutant deleted in the PK domain of the large subunit of ribonucleotide reductase (ICP10)" Elsevier Vaccine 17 (1999) 1951-1963.

Bateman, A., et al., "Fusogenic membrane glycoproteins as a novel class of genes for the local and immune-mediated control of tumor growth," Cancer Research, vol. 60, pp. 1492-1497 (Mar. 2000).

Browne, Helena, et al., "Plasma membrane requirements for cell fusion induced by herpes simplex virus type 1 glycoproteins gB, gD, gH and gL," Journal of General Virology (2001), 82, 1419-1422. Printed in Great Britain.

Carbone et al., Seminars in Cancer Biology, 2004, 14: 399-405.

Colunga, AG et al., "The HSV-2 mutant PK induces melanoma oncolysis through nonredundant death programs and associated with autophagy and pyroptosis proteins," Gene Therapy, No. 17, pp. 315-327 (2010).

Connor, Joe, "The unique N terminus of herpes simplex virus type 1 ribonucleotide reductase large subunit is phosphorylated by casein kinase 2, which may have a homologue in *Escherichia coli*," Journal of General Virology (1999), 80, 1471-1476. Printed in Great Britain.

Diaz, R.M., et al., "A lentiviral vector expressing a fusogenic glycoprotein for cancer gene therapy," Gene Therapy, vol. 7(19), pp. 1656-1663 (Oct. 2000).

Downward, Nat. Rev. Cancer, 2003 3: 11-22.

Foster, Timothy P., et al., "The Herpes Simplex Virus Type 1 UL20 Protein Modulates Membrane Fusion Events during Cytoplasmic Virion Morphogenesis and Virus-Induced Cell Fusion," Journal of Virology, vol. 78, No. 10, pp. 5347, 2004.

Fu, X., et al., "A strict-late viral promoter is a strong tumor-specific promoter in the context of an oncolytic herpes simplex virus," Gene Therapy, vol. 10(17), pp. 1458-1464 (Aug. 2003).

Fu, X. "A mutant type 2 herpex simplex virus deleted for the protein kinase domain of the ICP10 gene is a potent oncolytic virus," Molecular Therapy, vol. 13(5), pp. 882-890 (May 2006).

(Continued)

*Primary Examiner* — Anoop K Singh

(74) *Attorney, Agent, or Firm* — Blank Rome LLP

(57) ABSTRACT

The present invention is directed to the composition and use of a modified Herpes Simplex Virus Type 2 (HSV-2) as a medicament in the treatment of cancer. The modified HSV-2 has fusogenic activity, and comprises a modified/mutated ICP10 polynucleotide encoding a polypeptide having ribonucleotide reductase activity and lacking protein kinase activity.

7 Claims, 8 Drawing Sheets

(56) References Cited

OTHER PUBLICATIONS

Fu, X., et al., "Effective treatment of pancreatic cancer xenografts with a conditionally replicating virus derived from type 2 herpes simplex virus," Clinical Cancer Research, vol. 12(10), pp. 3152-3157 (May 15, 2006).
Fu, X., et al., "Expression of a fusogenic membrane glycoprotein by an oncolytic herpes simplex virus potentiates the viral antitumor effect," Molecular Therapy, vol. 7(6), pp. 748-754 (Jun. 2003).
Galanis, E., et al., "Use of viral fusogenic membrane glycoproteins as novel therapeutic transgenes in gliomas," Human Gene Therapy, vol. 12, pp. 811-821 (May 2001).
Gober, M.D., et al., "The growth compromised HSV-2 mutant ΔRR prevents kainic acid-induced apoptosis and loss of function in organotypic hippocampal cultures," Brain Research, vol. 11 19, pp. 26-39, Oct. 2006.
Higuchi, H., et al., "Viral fusogenic membrane glycoprotein expression causes syncytia formation with bioenergetic cell death: implications for gene therapy," Cancer Research, vol. 60(22), pp. 6396-3402 (Nov. 2000).
Hoggan, et al., Am. J. Hyg., 70: 208-219, 1959.
Hunter, J. C. R., "Intracellular internalization and signaling pathways triggered by the large subunit of HSV-2 ribonucleotide reducatse (ICP10)," Virology, 1995, 345-360, 210.
Hutchinson, L., et al., "Herpes simplex virus glycoprotein K is known to influence fusion of infected cells, yet is not on the cell surface," Journal of Virology, vol. 69, No. 7, pp. 4556-4563, 1995.
International Preliminary Report on Patentability dated Mar. 17, 2009, during the prosecution of International Application No. PCT/US2006/024440. Published Mar. 17, 2009.
Jesko Hars, Supplemental European Search Report, dated Oct. 20, 2010.
Jorgensen, T.J., et al., "Ionizing radiation does not alter the antitumor activity of herpes simplex virus vector G207 in subcutaneous models of human and murine prostate cancer," Neoplasia, vol. 3(5), pp. 451-456 (2001).
Kelland, et al., European Journal of Canber, 2004, 40, 827-836.
Kerbel, et al., Cancer Biology & Therapy 2:4 suppl. 1, S134-139, 2003.
Kunz-Schughart, et al., Journal of Biomolecular Screening, 2004, 9:273-285.
Langelier, Yves, et al., "The R1 Subunit of Herpes Simplex Virus Ribonucleotide Reductase is a Good Substrate for Host Cell Protein Kinases but is Not Itself a Protein Kinase," The Journal of Biological Chemistry, vol. 273, No. 3, Issue of Jan. 16, pp. 1435-1443, 1998.
Langelier, Yves, et al., "The ribonucleotide reducatse domain of the R1 subunit of herpes simplex virus type 2 ribonucleotide reductase is essential for R1 antiapoptotic function," Journal of General Virology (2007), 88, 384-394.
Luo, Jian-Hua, et al., "The Transmembrane Helical Segment but Not the Invariant Lysine is Required for the Kinase Activity of the Large Subunit of Herpes Simplex Virus Type 2 Ribonucleotide Reductase (ICP10)," The Journal of Biological Chemistry, vol. 267, No. 14, Issue of May 15, pp. 9645-9653, 1992.
Mantwill, K., et al., "Inhibition of the multidrug-resistant phenotype by targeting YB-1 with a conditionally oncolytic adenovirus: Implications for combinatorial treatment regimen with chemotherapeutic agents," Cancer Research, vol. 66(1), pp. 7195-7202 (Jul. 2006).
Martuza, R.L., "Conditionally replicating herpes vectors for cancer therapy," Journal of Clinical Investigation, vol. 105 (7), pp. 841-846 (Apr. 2000).
Mineta, et al., Nat. Med. 1995, 1, 938-943.
Mineta, T., et al., "Treatment of Malignant Gliomas Using Ganciclovir-hypersensitive, Ribonucleotide Reductase-deficient Herpes Simplex Viral Mutant," Cancer Research 54, pp. 3963-3966 (Aug. 1, 1994).
Muggeridge, M.I., "Characterization of cell-cell fusion mediated by herpes simplex virus 2 glycoproteins gB, gD, gH, and gL in transfected cells," Journal of General Virology, vol. 81)8_, pp. 2017-2027 (Aug. 2000).
Nakamori, M., et al., "effective therapy of metastatic ovarian cancer with an oncolytic herpes simplex virus incorporating two membrane fusion mechanisms," Clinical Cancer Research, vol. 9(7), pp. 2727-2733 (Jul. 2003).
Nakamori, M., et al., "Potent antitumor activity after systemic deliver of a doubly fusogenic oncolytic herpes simplex virus against metastatic prostate cancer," Prostate, vol. 60(1) (Jun. 2004).
Oshima, Tsutomu, et al., "Nectin-2 is a potential target for antibody therapy of breast and ovarian cancers," Obtained from http://www.molecular-cancer.com/content/12/1/60, Date retrieved Jun. 21, 2013, 13 pages.
Perkins, D., "The HSV2 R1 protein kinase (ICP10 PK) blocks apoptosis in hippocampal neurons," J. Virology, Feb. 2002, 1435-1449, vol. 76, No. 3.
Peng, Tao, et al., "The Novel Protein Kinase of the RR1 Subunit of Herpes Simplex Virus Has Autophosphorylation and Transphosphorylation Activity That Differs in Its ATP Requirements for HSV-1 and HSV-2," Virology, 216, pp. 184-196, 1996.
Read, et al., J. Virol., 35: 105-113, 1980.
Smith, C. C., et al., "Ras-GAP Binding and Phosphorylation by Herpes Simplex Virus Type 2 RR1 PK (ICP10) and Activation of the RAS/MEK/MAPK Mitogenic Pathway are Required for Timely Onset of Virus Growth," Journal of Virology, vol. 74, No. 22, pp. 10417-10429, 2000.
Smith, C.C., et al., "The PK Domain of the Large Subunit of Herpes Simplex Virus Type 2 Ribonucleotide Reductase (ICP10) is Required for Immediate-Early Gene Expression and Virus Growth," Journal of Virology, pp. 9131-9141 (Nov. 1998).
Smith, C.C. et al., "The large subunit of herpes simplex virus type 2 ribonucleotide reductase (ICP10) is associated with the virion tegument and has PK activity," Virology vol. 234, pp. 235-242 (1999).
Smith, C.C., et al., "The transmembrane domain of the large subunit of HSV-2 ribonucleotide reductase (ICP10) is required for protein kinase activity and transformation-related signaling pathways that result in ras activation," Virology, vol. 200, pp. 598-612 (1994).
Takai, Yoshimi, et al., "Nectin and afadin: novel organizers of intercellular junctions," Journal of Cell Science, 116, pp. 17-27, 2003.
Terry-Allison, Tracy, et al., "Contributions of gD receptors and glycosaminoglycan sulfation to cell fusion mediated by herpes simplex virus 1," Virus Research, 74, pp. 39-45, 2001.
Wales, Samantha, The HSV2 gene ICP10PK protects from apoptosis causes by NGF deprivation through inhibition of caspase-3 activation, J. Neurochem., 2007, 365-379, 103(1).
Walker, J.R., et al., "Local and systemic therapy of human prostate adenocarcinoma with the conditionally replicating herpes simplex virus vector G207," Human Gene Therapy, vol. 10(13), pp. 2237-2242 (Sep. 1, 1999).
Wang, Yu-Chun, "A cell line that secretes inducibly a reporter protein for monitoring herpes simplex virus infection and drug susceptibility," J. Med. Virology, 2002, 599-605, 68.
Weinheimer, Steven P., "Transcriptional and post-transcriptional controls establish the cascade of herpes simplex virus protection synthesis," J. Mol. Biol, 1986, 195, 819-833.
Yamamoto, S., et al., "Imaging immediate-early and strict-late promoter activity during oncolytic herpes simplex virus type 1 infection and replication in tumors," Gene Therapy, vol. 13(24), pp. 1731-1736 (Dec. 2006).
Yu, Zhenkun, et al., "Nectin-1 Expression by Squamous Cell Carcinoma is a Predictor of Herpes Oncolytic Sensitivity," Molecular Therapy, vol. 15, No. 1, pp. 103-113, 2007.

* cited by examiner

TR
ICP10
IR
TR

PK
ICP10 promoter
PK domain
RR domain
BamHI
BamHI

PKL
GFP
PKR
CMV promoter
EGFP gene
RR domain
BamHI
BamHI
BamHI

PBS

Baco-1

FusOn-H2

MUTANT HERPES SIMPLEX VIRUS-2 FOR CANCER THERAPY

CROSS-REFERENCES TO RELATED APPLICATIONS

This application is a divisional of U.S. application Ser. No. 11/922,796, filed Aug. 6, 2008, which is a national stage application of International Application number PCT/US2006/024440, filed Jun. 23, 2006, which claims priority to provisional application No. 60/693,157, filed on Jun. 23, 2005, all of which are herein incorporated by reference in their entirety.

STATEMENT AS TO RIGHTS TO INVENTIONS MADE UNDER FEDERALLY SPONSORED RESEARCH OR DEVELOPMENT

This invention was made with government support under grant number RO1 CA 106671-01 awarded by the NIH. The government may have certain rights in the invention.

FIELD OF THE INVENTION

The present invention is directed to the fields of virology, cancer biology, cell biology, molecular biology, and medicine, including cancer therapeutics. Specifically, the present invention provides a mutant Herpes Simplex Virus-2 (HSV-2) comprising a modification of the ICP10 gene and the use of this mutant HSV-2 for the treatment of malignant diseases.

BACKGROUND OF THE INVENTION

Replication selective oncolytic viruses have shown great promise as anti-tumor agents for solid tumors. These viruses are able to preferentially replicate within tumor cells, while being restricted in their ability to replicate in normal cells. The principle anti-tumor mechanism of oncolytic viruses is through a direct cytopathic effect as they propagate and spread from initially infected tumor cells to surrounding tumor cells, achieving a larger volume of distribution and anticancer effects. Herpes simplex virus (HSV) has been modified for oncolytic purposes, most commonly by deleting viral genes necessary for efficient replication in normal (non-dividing) cells but not tumor cells. The modifications include deletion of either the viral γ34.5 gene or ICP6 gene. The viral γ34.5 gene functions as a neurovirulence factor during HSV infection (Chou, et al, (1990) *Science* 250: 1262-1266). Deletion of this gene blocks viral replication in non-dividing cells (McKie, et al., (1996) *Br J Cancer* 74(5): 745-52). The viral ICP6 gene encodes the large subunit of ribonucleotide reductase, which generates sufficient dNTP pools for efficient viral DNA replication and is abundantly expressed in tumor cells but not in non-dividing cells. Consequently, viruses with a mutation in this gene can preferentially replicate in—and kill—tumor cells. The oncolytic HSV G207, which has been extensively tested in animal studies and is currently in clinical trials, harbors deletions in both copies of the γ34.5 locus and an insertional mutation in the ICP6 gene by the *E. coli* lacZ gene (Walker, et al., (1999) *Human Gene Ther.* 10(13):2237-2243). Alternatively, an oncolytic type-1 HSV can be constructed by using a tumor-specific promoter to drive γ34.5 or other genes essential for HSV replication (Chung, et al., (1999) *J Virol* 73(9): 7556-64).

Oncolytic herpes simplex viruses (HSV) were initially designed and constructed for the treatment of brain tumors (Andreansky, et al., (1996) *Proc Natl Acad. Sci.* 93(21): 11313-11318). Subsequently, they have been found to be effective in a variety of other human solid tumors, including breast (Toda, et al., (1998) *Human Gene Ther.* 9(15):2177-2185), prostate (Walker, et al., (1999) *Human Gene Ther.* 10(13):2237-2243) lung (Toyoizumi, et al., (1999) *Human Gene Ther.* 10(18):3013-3029), ovarian (Coukos, et al., (1999) *Clin. Cancer Res.* 5(6):1523-1527), colon and liver cancers (Pawlik, et al., (2000) *Cancer Res.* 61(11):2790-2795). The safety of oncolytic HSVs has also been extensively tested in mice (Sundaresan, et al., (2000) *J. Virol.* 74(8):3832-3841) and primates (Aotus), which are extremely sensitive to HSV infection (Todo, et al., (2000) *Cancer Gene Ther.* 7(6):939-946). These studies have confirmed that oncolytic HSVs are extremely safe for in vivo administration.

Oncolytic HSVs have been exclusively constructed from HSV-1. HSV-2 has not been explored for the purpose of constructing oncolytic viruses. Nonetheless, HSV-2 has some unique features that enhance its potential as an oncolytic agent. For example, it has been reported that, unlike HSV-1, HSV-2 encodes a secreted form of glycoprotein G (gG) that affects the function of neutrophils, monocyte and NK cells (Bellner, et al. (2005) *J Immunol* 174(4): 2235-41). Such a property may provide an oncolytic virus derived from HSV-2 with the ability to resist the inhibitory effect of the body's innate immunity. Innate immunity is a quick response of the host to invading microorganisms and it has been found to be the major factor that restricts HSV replication in vivo (Dalloul, et al., (2004) *J Clin Virol* 30(4): 329-36; Wakimoto, et al., (2003) *Gene Ther* 10(11):983-90. Thus, an oncolytic virus derived from HSV-2 should replicate and spread even when the patient's body develops anti-HSV innate immunity.

Despite encouraging preclinical studies, results from early clinical trials have suggested that the current versions of oncolytic viruses, although safe, may only have limited anti-tumor activity on their own (Nemunaitis, et al., (2001) *J. Clin Oncol.* 19(2):289-298). Studies from the inventors' work have demonstrated that incorporation of cell-membrane fusion activity into an oncolytic HSV can dramatically improve the anti-tumor potency of the virus (Fu, et al., (2002) *Mol. Ther.* 7(6): 748-754; Fu, et al., (2003) *Cancer Res.* 62: 2306-2312. Such fusogenic oncolytic viruses produce syncytial formation in the tumor, directly enhancing the destructive power of the virus and promoting its intratumor spread (Fu, et al., (2003) *Cancer Res.* 62: 2306-2312). The uniquely combined tumor-destruction mechanism of syncytial formation and direct cytolysis by the fusogenic oncolytic HSV also facilitates in situ tumor antigen presentation, leading to potent anti-tumor immune responses (Nakamori, et al., (2004) *Mol. Ther.* 9(5): 658-665). Furthermore, the spread of a fusogenic oncolytic HSV through syncytial formation will allow it to maintain its anti-tumor activity even in the presence of neutralizing anti-viral antibodies in the host. Viruses can only replicate inside living cells and their replication usually requires activation of certain cellular signaling pathways. Many viruses have acquired various strategies during their evolution to activate these signaling pathways to benefit their replication. The large subunit of herpes simplex virus type 2 (HSV-2) ribonucleotide reductase (ICP10 or RR1) contains a unique amino-terminal domain which has serine/threonine protein kinase (PK) activity. This PK activity has been found to activate the cellular Ras/MEK/MAPK pathway (Smith, et al., (2000) *J Virol* 74(22): 10417-29).

Luo and Aurelian describe various vectors comprising different deletions of the ICP10 gene in HSV-2 to demonstrate the relationship between particular motifs and certain activities (Luo and Aurelian, (1992) *J Biol Chem* 267(14): 9645-53). Modified and deletion constructs of the HSV-2 ICP10 gene have been used to demonstrate particular characteristics of the ribonucleotide reductase domain (Peng et al. (1996) *Virology* 216(1): 184-96).

Deletion of the PK domain (ICP10 PK) from the ribonucleotide reductase gene severely compromises the ability of the virus to replicate in cells where there is no preexisting activated Ras signaling pathway (Smith et al (1998) *J. Virol.* 72(11):9131-9141).

U.S. Pat. No. 6,013,265 is directed to a vaccine that provides protection from challenge by HSV-2, wherein the protein kinase domain of ICP10 has been deleted, which leads to deleterious effects on the ability of HSV-2 to infect and transform cells.

The present invention fulfills a need in the art by providing novel therapeutics for the treatment of cancer utilizing a modified HSV-2.

BRIEF SUMMARY OF THE INVENTION

The present invention addresses a long-felt need in the art by providing a potent modified Herpes Simplex Virus Type 2 (HSV-2), having oncolytic properties. In specific embodiments of the invention, the virus has a modified ICP10 polynucleotide that encodes for an ICP10 polypeptide that has ribonucleotide reductase activity, but lacks protein kinase activity. In particular aspects, the virus is useful for therapy of malignant cells. In specific embodiments, the virus replicates selectively in tumor cells. In further specific embodiments, the virus generates cell membrane fusion to rid a culture, tissue, or organism of at least some undesirable cells. In still further specific embodiments, the virus inhibits proliferation of at least some undesirable cells, and/or induces apoptosis in at least some desirable cells, and/or induces a strong anti-tumor immune response, and/or a combination thereof.

The native HSV-2 virus comprises an ICP10 polynucleotide (which may also be referred to as an RR1 polynucleotide) encoding a polypeptide having an amino-terminal domain with protein kinase (PK) activity, such as serine/threonine protein kinase activity and a c-terminal domain having ribonucleotide reductase activity. In particular aspects of the invention, the endogenous PK domain is modified such that the virus comprises selective replication activity in tumor cells (and therefore comprises activity to destroy tumor cells) and/or activity to render the virus fusogenic or have enhanced fusogenic activity, in that it comprises membrane fusion (syncytial formation) activity. In some embodiments, the ICP10 polynucleotide is modified by deleting at least part of the endogenous sequence encoding the protein kinase domain, such that the encoded polypeptide lacks protein kinase activity.

In another embodiment of the invention, a second polynucleotide replaces at least part of an endogenous ICP10 polynucleotide encoding for at least part of the protein kinase domain. In yet other embodiments, the ICP10 sequence that was not replaced comprises the entire RR domain. The replacement of at least part of the endogenous ICP10 polynucleotide may occur through any suitable method, such as for example, by homologous recombination or other suitable genetic engineering methods, including the use of PCR and other methodologies as are well known to persons of skill in the art.

In additional aspects of the invention, the polynucleotide that replaces at least part of the endogenous PK domain of ICP10 may be of any suitable sequence. For example, the polynucleotide that replaces the PK domain may encode a reporter gene product or a therapeutic gene product. The modified ICP10 polynucleotide containing the second polynucleotide (that replaced at least a portion of the PK domain) will encode for a fusion protein comprised of the replacement polynucleotide and the remaining non-replaced portion of the ICP10 gene. Non-limiting examples of reporter genes that are suitable for use with the present invention include green fluorescent protein (SEQ ID NO:16; GenBank Accession No. U55761), β-galactosidase, luciferase, and Herpes simplex virus thymidine kinase (HSV-tk). Non-limiting examples of therapeutic polynucleotides may include Herpes simplex virus thymidine kinase (HSV-tk), cytosine deaminase, caspase-3, and wild-type p53.

In still other embodiments of the invention, the polynucleotide that replaces at least part of the endogenous PK domain of ICP10 may be an immunomodulatory gene, or a polynucleotide that encodes for a fusogenic membrane glycoprotein (FMG). Non-limiting examples of immunomodulatory genes that are suitable for use with the present invention include IL-2, IL-12, or GM-CSF, and other cytokines; F42K and other cytokine analogs; or MIP-1, MIP-1 beta, MCP-1, RANTES, and other chemokines Non-limiting examples of polynucleotides encoding fusogenic membrane glycoproteins that are suitable for use with the present invention include paramyxovirus F protein, HIV gp160 protein, SIV gp160 protein, retroviral Env protein, Ebola virus Gp, or the influenza virus haemagglutinin, a membrane glycoprotein from gibbon ape leukemia virus (GALV) or a C-terminally truncated form of the gibbon ape leukemia virus envelope glycoprotein (GALV.fus).

In other embodiments of the invention, the modified ICP10 polynucleotide is operably linked to a constitutive promoter. Non-limiting exemplary constitutive promoters that are suitable for use with the present invention include the immediate early cytomegalovirus (CMV) promoter, SV40 early promoter, RSV LTR, Beta chicken actin promoter, and HSV0-TK promoter. In other embodiments of the invention, the polynucleotide that replaces at least part of the endogenous PK domain (or TM domain) comprises a regulatory sequence operably linked thereto. The regulatory sequence is operable in a eukaryotic cell, in specific embodiments, and in further aspects is operable in a cancer cell. Non-limiting exemplary promoters useful for practicing the methods and compositions described herein may include tumor-specific promoters and/or tissue-specific promoters, e.g., prostate-specific antigen (PSA) promoter, kallikrein 2 promoter and probasin promoter (for prostate cancer), L-plastin promoter (for cancers of the breast, ovary and colon), thyroglobulin core promoter (for thyroid carcinomas), Midkine and cyclooxygenase 2 promoters (for pancreatic carcinoma), and human telomerase promoter (hTERT) for the majority of tumors.

In a further embodiment, there is provided a method of generating fusion between a first cell and a second cell, comprising the step of fusing the second cell membrane with the first cell membrane by introducing to the first cell a composition of the invention. In specific embodiments, the first cell, second cell, or both first and second cells are malignant cells, such as those in a solid tumor. Non-limiting examples of malignant cells suitable for use in practicing the methods and compositions described herein may include breast cancer cells, lung cancer cells, skin cancer cells, prostate cancer cells, pancreatic cancer cells, colon cancer cells, brain cancer cells, liver cancer cells, thyroid cancer cells, ovarian cancer cells, kidney cancer cells, spleen cancer cells, leukemia cells, or bone cancer cells.

In specific embodiments the introducing step is further defined as delivering the virus to the human, such as by systemically delivering the virus to the human. Non-limiting routes of administration may include administering the compositions described herein intravenously, intratumorally, intraperitoneally, or any combination thereof. In specific embodiments, the composition is introduced to a plurality of cells.

In an additional embodiment, there is provided a method of destroying a malignant cell, such as one in a human, comprising the step of introducing to the cell a composition of the invention, wherein following said introduction the membrane of the malignant cell fuses with another cell membrane.

In another embodiment, there is a mammalian cell comprising a composition of the invention. The mammalian cell may be a normal lymphocyte, macrophage, natural killer cell or any other type of cell that may function as a carrier to send the composition of the invention to a tumor cell.

In yet another embodiment of the present invention, the modified HSV-2 virus or viral vector as described herein induces apoptosis in cancer cells infected with the virus. In yet another embodiment, apoptosis is induced in bystander cells which are not infected with the virus, but surround cells that are infected with the modified HSV-2 virus described herein.

In yet another embodiment of the invention, a virus or viral vector as described herein comprises part of a system for assaying the efficacy of the virus for lysing cells and or syncytial formation. The system comprises a cell contacted with a virus or vector as described herein. In some embodiments, the cell may be a eukaryotic cell, such as a primary cancer cell, or a cell from a cancer cell line. In other embodiments, the cell may be a prokaryotic cell that serves as host for the virus or vector as described herein. In still other embodiments of the invention, the cell further comprising the virus or viral vector, may be maintained in vitro. In still other embodiments of the invention, the cell further comprising the virus or vector is placed into an animal, such as a mouse. In still other embodiments of the invention, the cancer cell can be transplanted into an animal prior to being placed in contact with the virus or vector.

The foregoing has outlined rather broadly the features and technical advantages of the present invention in order that the detailed description of the invention that follows may be better understood. It will be appreciated by those skilled in the art that the conception and specific embodiments disclosed may be readily utilized as a basis for modifying or designing other structures for carrying out the same purposes of the present invention. It will also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying examples and figures. It is to be expressly understood, however, that each of the examples and figures is provided for the purpose of illustration and description only and is not intended as a definition of the limits of the present invention.

BRIEF DESCRIPTION OF THE DRAWINGS

FIG. 1A. Schematic representation of HSV-2 genome. The genome is represented by a gray bar, while the terminal repeats (TR) and internal repeats (IR) are shown as gray boxes. The location of ICP10 gene is also indicated. FIG. 1B. Enlarged view of the ICP10 gene, showing the positions of the PK and RR1 domains and the natural promoter. FIG. 1C. Modified ICP10 gene, which was subsequently inserted into the viral genome to construct FusOn-H2. As shown, the PK domain was replaced with the EGFP gene (in frame with the RR gene), and the original promoter of the gene was replaced with the immediate early promoter of cytomegalovirus, one of the strongest mammalian gene promoters. The BamHI restriction sites in the unmodified and the modified ICP10 locus are labeled. The boxes labeled as PKL, PK, GFP and PKR indicate the locations where the 4 probes used in the Southern hybridization in FIG. 2 will hybridize to.

FIG. 5A. Vero cells were maintained in fully cycling state (10% FBS) or were starved for serum for 24 h before they were infected with the viruses at 1 pfu/cell. Cells were harvested at the indicated time points and the virus yield was quantified by plaque assay on Vero cell monolayers. FIG. 5B. Vero cells were incubated in medium containing a low percentage of serum (2%) alone or in the presence of 50 μM PD98059 during the virus infection. Cells were harvested at 24 h and 48 h after infection, and the fold reduction in virus replication was calculated by dividing the total virus yield in the well without PD98059 by that from the well containing the drug. FIG. 5C. Primary hepatocytes cultured in vitro were infected with the indicated viruses at 1 pfu/cell. The viruses were harvested at the indicated times after infection and quantified by plaque assay on Vero cell monolayers. *$p<0.01$, FusOn-H2 compared with wt186 (Student's t-test).

FIG. 7A. Therapeutic effect after intra-tumor delivery. Human breast tumor xenografts were established by injecting MDA-MB-435 cells into the fat part of the second mammary. When tumors reached about 5 mm in diameter, viruses were injected intratumorally at a dose of $1\times10^6$ pfu. Treatment groups include FusOn-H2, Baco-1, or PBS. The tumor growth ratio was determined by dividing the tumor volume measured on the indicated week after virus injection by the tumor volume before treatment (n=8 mice per group). FIG. 7B. Therapeutic effect against large breast tumor xenografts. Tumors were 10 and 10-15 mm in diameter, respectively, for intra-tumor and intravenous injection groups (n=5 each). For intra-tumor and intravenous injections, viruses were given at doses of $3\times10^6$ pfu and $1.5\times10^7$ pfu, respectively. The tumor growth ratio was calculated in the same way as in FIG. 6A. $^{\Psi}p<0.05$, FusOn-H2 compared with Baco-1; $^{*}p<0.01$, FusOn-H2 compared with Synco-2D (Student's t-test).

DETAILED DESCRIPTION OF THE INVENTION

Figures 1A, 1B, 1C:
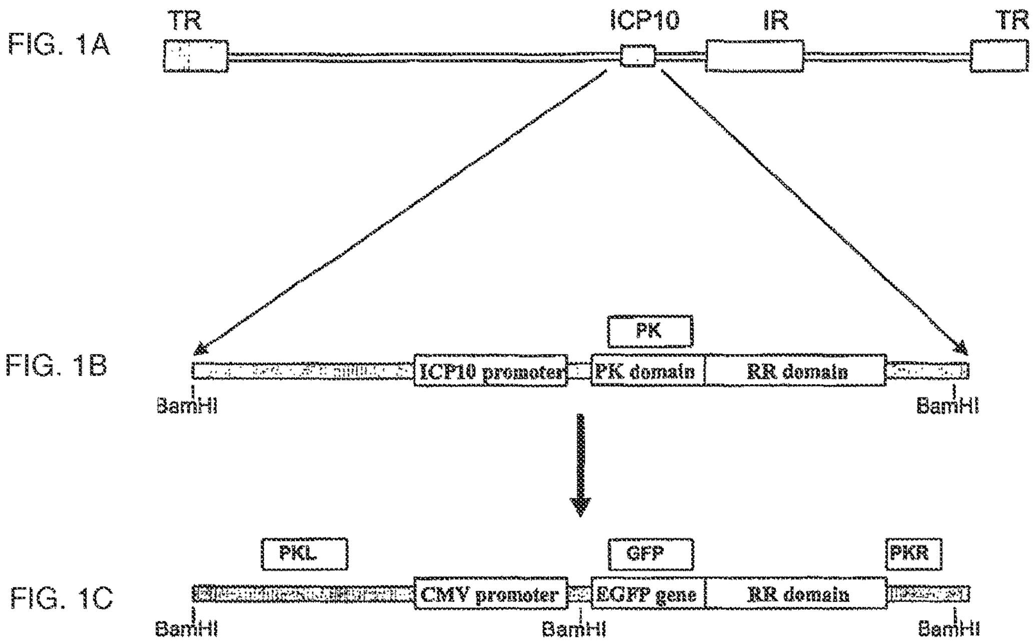
FIGS. 1A, 1B, and 1C shows the strategy for FusOn-H2 construction.

The HSV-2 viral composition as described in Example 1, was deposited on Jun. 8, 2006, with the American Type Culture Collection (ATCC) 10801 University Blvd. Manassas, Va. 20110-2209 USA. The ATCC is an International Depository Authority (IDA) as established under the Budapest Treaty. The certificate of deposit number is PTA-7653.

I. Definitions

The term "Herpes Simplex Virus" or "HSV" as used herein refers to an enveloped, icosahedral, double-stranded DNA virus that infects mammals, including humans. Wild-type HSV infects and replicates in both terminally differentiated non-dividing cells and dividing cells. "HSV-2" refers to a member of the HSV family that contains the ICP10 gene. The term "FusOn-H2" as used herein refers to a HSV-2 mutant having a modified ICP10 polynucleotide encoding a polypeptide having ribonucleotide reductase activity, but lacking protein kinase activity as described herein.

The term "cell membrane fusion" as used herein refers to fusion of an outer membrane of at least two cells, such as two adjacent cells, for example.

The term "enhanced fusogenic activity" as used herein refers to an enhancement, increase, intensification, argumentation, amplification, or combination thereof of the cell membrane fusion.

The term "oncolytic" as used herein refers to a property of an agent that can result directly or indirectly, in the destruction of malignant cells. In a specific embodiment, this property comprises causing fusion of a malignant cell membrane to another membrane.

The term "replication selective" or "replication conditional" as used herein refers to the ability of an oncolytic virus to selectively grow in certain tissues (e.g., tumors).

The term "syncytium" as used herein refers to a multinucleate giant cell formation involving a significantly larger number of fused cells.

The term "vector" as used herein refers to a carrier nucleic acid molecule into which a nucleic acid sequence can be inserted for introduction into a cell where it can be replicated. The inserted nucleic acid sequence is referred to as "exogenous" either when it is foreign to the cell into which the vector is introduced or when it is homologous to a sequence in the cell but in a position within the host cell nucleic acid in which die sequence is ordinarily not found. A vector can be either a non-viral DNA vector or a viral vector. Viral vectors are encapsulated in viral proteins and capable of infecting cells. non-limiting examples of vectors include: a viral vector, a non-viral vector, a naked DNA expression vector, a plasmid, a cosmid, an artificial chromosome (e.g., YACS), a phage-vector, a DNA expression vector associated with a cationic condensing agent, a DNA expression vector encapsulated in a liposome, or a certain eukaryotic cell e.g., a producer cell. Unless stated otherwise, "vector" as used herein refers both a DNA vector and a viral vector. One of skill in the art would be well equipped to construct a vector through standard recombinant techniques. Generally, these include Sambrook et al., *Molecular Cloning: A Laboratory Manual,* 2nd Ed., Cold Spring Harbor Laboratory Press (1989) and the references cited therein. Virological considerations are also reviewed in Coen D. M, *Molecular Genetics of Animal Viruses in Virology,* $2^{nd}$ Edition, B. N. Fields (editor), Raven Press, N.Y. (1990) and the references cited therein.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind, such as RNA polymerase and other transcription factors to initiate or regulate the temporal and spatial transcription of a nucleic acid sequence. The phrases "operatively positioned," "operably linked," "under control," and "under transcriptional control" mean that a promoter is in a correct functional location and/or orientation in relation to a nucleic acid sequence to control transcriptional initiation and/or expression of that sequence. Exemplary non-limiting promoters include: a constitutive promoter, a tissue-specific promoter, a tumor-specific promoter, or an endogenous promoter under the control of an exogenous inducible element.

The term "constitutive promoter" as used herein refers to a promoter that drives expression of a gene or polynucleotide in a continuous temporal manner throughout the cell cycle. A constitutive promoter may be cell or tissue-type specific as long as it operates in a continuous fashion throughout the cell cycle to drive the expression of the gene or polynucleotide with which it is associated. Exemplary non-limiting constitutive promoters include: the immediate early cytomegalovirus (CMV) promoter, SV40 early promoter, RSV LTR, Beta chicken actin promoter, and HSV TK promoter.

The term "enhancer" refers to a cis-acting regulatory sequence involved in the control of transcriptional activation of a nucleic acid sequence.

The terms "contacted" and "exposed," when applied to a cell are used herein to describe the process by which a virus, viral vector, non-viral vector, DNA vector, or any other therapeutic agent, alone or in combination, is delivered to a target cell or placed in direct juxtaposition with a target cell.

The phrase "modified ICP10 polynucleotide" refers to an ICP10 polynucleotide that encodes for an ICP10 polypeptide that has ribonucleotide reductase (RR) activity, but lacks protein kinase activity.

The phrase "ribonucleotide reductase activity" refers to ability of the C-terminal domain of the polypeptide encoded by an ICP10 polynucleotide to generate sufficient deoxynucleotide triphosphates (dNTPs) required for viral replication.

The phrase "protein kinase activity" refers to the ability of the amino-terminal domain of the polypeptide encoded by an ICP10 polynucleotide to phosphorylate serine and threonine residues capable of activating the Ras/MEK/MAPK pathway.

The term "by-stander tumor cell" as used herein refers to tumor cells that are not infected with a modified HSV-2 virus as described herein, but are adjacent to or near tumor cells that are infected with a virus or vector as described herein.

The term "anti-cancer agent" as used herein refers to an agent that is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The phrases "pharmaceutically" or "pharmacologically acceptable" as used herein refer to molecular entities and compositions that do not produce an adverse, allergic or other untoward reaction when administered to an animal, or human, as appropriate. The phrase "pharmaceutically acceptable carrier" includes any and all solvents, dispersion media, coatings, antibacterial and antifungal agents, isotonic and absorption delaying agents and the like.

The term "unit dose" refers to a physically discrete unit suitable for use in a subject, each unit containing a predetermined quantity of the therapeutic composition calculated to produce the desired response in association with its administration, i.e., the appropriate route and treatment regimen.

The term "effective" or "therapeutically effective" as used herein refers to inhibiting an exacerbation in symptoms, preventing onset of a disease, preventing spread of disease, amelioration of at least one symptom of disease, or a combination thereof.

II. Introduction

Viruses can only replicate inside living cells and their replication usually requires activation of certain cellular signaling pathways. Many viruses have acquired various strategies during their evolution to activate these signaling pathways to benefit their replication. The large subunit of herpes simplex virus type 2 (HSV-2) ribonucleotide reductase (ICP10 or RR1) comprises a unique amino-terminal domain that has serine/threonine protein kinase (PK) activity. This PK activity has been found to activate the cellular Ras/MEK/MAPK pathway (Smith, et al., (2000) *J Virol* 74(22): 10417-29). Consequently, it has been reported that deletion of this PK domain (ICP10 PK) from the ribonucleotide reductase gene severely compromises the ability of the virus to replicate in cells, such as those where there is no preexisting activated Ras signaling pathway (Smith, et al., (1998) *J. Virol.* 72(11):9131-9141).

Here, the present inventors show that when the PK domain of HSV-2 is replaced and/or modified such that protein encoded by the modified ICP10 gene has ribonucleotide reductase activity, but lacks protein kinase activity, the virus selectively replicates in and destroys tumor cells (at least tumor cells in which the Ras signaling pathway is constitutively activated due to tumorigenesis). Furthermore, modification of the ICP10 polynucleotide as described herein renders the virus intrinsically fusogenic, i.e., infection of tumor cells with the virus induces widespread cell membrane fusion (syncytial formation). This property increases the destructive power of the virus against tumor cells. Furthermore, in vivo studies show that this virus is extremely safe for either local or systemic administration.

In some embodiments of the invention, the modification of the PK domain comprises insertion of a reporter gene, such as that expressing the green fluorescent gene, and/or replacement of the native promoter gene with a constitutive promoter, such as the immediate early cytomegalovirus promoter.

In some embodiments, the HSV-2 is genetically engineered either by inserting a second polynucleotide into the polynucleotide encoding the protein kinase activity domain of the ICP10 gene, or by replacing a portion of the protein kinase domain with a second polynucleotide such that the polypeptide encoded by the modified polynucleotide has ribonucleotide reductase activity, but lacks protein kinase activity. For example, the second polynucleotide may encode a glycoprotein, such as a fusogenic membrane glycoprotein. A preferred glycoprotein for use within the scope of the present invention is a truncated form of gibbon ape leukemia virus envelope fusogenic membrane glycoprotein (GALV.fus). In certain aspects of the invention, expression of GALV.fus in the context of the oncolytic virus of the present invention significantly enhances the anti-tumor effect of the virus.

In some embodiments, the modified HSV-2 of the invention comprises a mutation, such as a deletion, in ICP10 that provides cell fusogenic properties to the virus. Such a mutation may be generated randomly during the virus screening or obtained from nature, and a pool of potential candidates for having cell fusogenic properties is then assayed for the function by means described herein and/or known in the art. A mutation leading to the fusogenic phenotype may be a point mutation, a frame shift, an inversion, a deletion, a splicing error mutation, a post-transcriptional processing mutation, over expression of certain viral glycoproteins, a combination thereof, and so forth. The mutation may be identified by sequencing the particular HSV-2 and comparing it to a known wild type sequence.

The modified HSV-2 of the present invention is useful for the treatment of malignant cells, such as, for example, to inhibit their spread, decrease or inhibit their division, eradicate them, prevent their generation or proliferation, or a combination thereof. The malignant cells may be from any form of cancer, such as a solid tumor, although other forms are also treatable. The modified HSV-2 of the present invention is useful for the treatment of lung, liver, prostate, ovarian, breast, brain, pancreatic, testicular, colon, head and neck, melanoma, and other types of malignancies. The invention is useful for treating malignant cells at any stage of a cancer disease, including metastatic stages of the disease. The invention may be utilized as a stand-alone therapy or in conjunction with another means of therapy, including chemotherapy, surgery, radiation, and the like III. Modified ICP10 Polynucleotide The present invention describes a HSV-2 mutant having a modified ICP10 polynucleotide, wherein the modified ICP10 polynucleotide encodes for a polypeptide that has ribonucleotide reductase activity, but lacks protein kinase (PK) activity. The ICP10 polynucleotide may be modified either by deleting at least some of the sequence required for encoding a functional PK domain, or replacing at least part of the sequence encoding the PK domain with a second polynucleotide. One of skill in the art will recognize that any suitable method can be used for generating the modified ICP10 polynucleotide, including mutagenesis, polymerase chain reaction, homologous recombination, or any other genetic engineering technique known to a person of skill in the art.

A. Mutagenesis

In specific embodiments of the invention, an ICP10 sequence of an HSV-2 virus, is mutated, such as by deletion, using any of a variety of standard mutagenic procedures. Mutation can involve modification of a nucleotide sequence, a single gene, or blocks of genes. A mutation may involve a single nucleotide (such as a point mutation, which involves the removal, addition or substitution of a single nucleotide base within a DNA sequence) or it may involve the insertion or deletion of large numbers of nucleotides. Mutations can arise spontaneously as a result of events such as errors in the fidelity of DNA replication, or induced following exposure to chemical or physical mutagens. A mutation can also be site-directed through the use of particular targeting methods that are well known to persons of skill in the art.

B. Genetic Recombination

In other embodiments of the invention, the ICP10 polynucleotide is modified using genetic recombination techniques to delete or replace at least part of the sequence encoding for the PK domain. The region of the PK domain that is deleted/replaced may be any suitable region so long as the polypeptide encoded by the modified ICP10 polynucleotide retains ribonucleotide reductase activity and lacks protein kinase activity. In certain embodiments, though, the modification to the PK domain affects one or more of the eight PK catalytic motifs (amino acid residues 106-445, although the PK activity may be considered amino acid residues 1-445), and/or the transmembrane (TM) region, and/or the invariant Lys (Lys 176). An exemplary wild-type ICP10 polypeptide sequence is provided in SEQ ID NO:15 (National Center for Biotechnology Information's GenBank database Accession No. 1813262A). An exemplary wild-type polynucleotide that encodes an ICP10 polypeptide is provided in SEQ ID NO:17.

In certain embodiments, the ICP10 polynucleotide is modified by merely deleting a portion of the sequence encoding the PK domain that is necessary for PK activity. An exemplary ICP10 polynucleotide lacking at least some sequence that encodes a PK domain is provided in SEQ ID NO:18. In another exemplary embodiment, ICP10 polynucleotide is modified such that the PK domain is deleted in its entirety, as provided in SEQ ID NO:19. Both SEQ ID NO:18 and SEQ ID NO:19 are suitable for use in generating a HSV-2 mutant as described herein, as both sequences encode for polypeptides that have ribonucleotide reductase activity, but lack protein kinase activity. In certain embodiments of the invention, the modified ICP10 polynucleotide disclosed in SEQ ID NO:18 or SEQ ID NO:19 may be under the control of the endogenous HSV-2 promoter, or operably linked to a constitutive promoter, such as the immediate early cytomegalovirus promoter described in SEQ ID NO:20.

In still other embodiments of the invention, the ICP10 polynucleotide is modified by replacing at least part of the sequence encoding the PK domain with a second polynucleotide, such as green fluorescent protein, which is placed in frame with the sequence encoding the RR domain of the ICP10 polynucleotide. This construct can be either under control of the endogenous HSV-2 promoter, or under the control of a constitutive promoter such as the CMV promoter (SEQ ID NO:20). This latter construct (containing GFP replacement polynucleotide and the CMV promoter) is described in greater detail in Example 1.

In another aspect of the invention, the polynucleotide that replaces at least part of the protein kinase activity domain of the endogenous ICP10 in HSV-2 can encode at least a fusogenic portion of a cell membrane fusion-inducing polypeptide, such as a viral fusogenic membrane glycoprotein (FMG). The polypeptide is preferably capable of inducing cell membrane fusion at a substantially neutral pH (such as about pH 6-8), for example.

In particular embodiments, the FMG comprises at least a fusogenic domain from a C-type retrovirus envelope protein, such as MLV (as an example, SEQ ID NO:6) or GALV (as an example, SEQ ID NO:5). A retroviral envelope protein having a deletion of some, most, or all of the cytoplasmic domain is useful, because such manipulation results in hyperfusogenic activity for human cells. Particular modifications are introduced, in some embodiments, into viral membrane glycoproteins to enhance their function to induce cell membrane fusion. For example, truncation of the cytoplasmic domains of a number of retroviral and herpes virus glycoproteins has been shown to increase their fusion activity, sometimes with a simultaneous reduction in the efficiency with which they are incorporated into virions (Rein et al., (1994) *J Virol* 68(3): 1773-81).

Some examples of cell membrane fusing polypeptides include measles virus fusion protein (SEQ ID NO:7), the HIV gp160 (SEQ ID NO:8) and SIV gp160 (SEQ ID NO:9) proteins, the retroviral Env protein (SEQ ID NO:10), the Ebola virus Gp (SEQ ID NO:11), and the influenza virus haemagglutinin (SEQ ID NO:12).

In other embodiments, a second functional polynucleotide may be either inserted into the PK domain, or used to replace part or all of the PK domain. This second functional polynucleotide may encode for an immunomodulatory or other therapeutic agent. It is contemplated that these additional agents will affect the upregulation of cell surface receptors and GAP junctions, cytostatic and differentiation agents, inhibit cell adhesion, or increase the sensitivity of the malignant cells to apoptosis. Exemplary, non-limiting examples of polynucleotides encoding for immunomodulatory or other therapeutic agents include tumor necrosis factor; interferon, alpha, beta, gamma; interleukin-2 (IL-2), IL-12, granulocyte macrophage-colony stimulating factor (GM-CSF), F42K, MIP-1, MIP-1β, MCP-1, RANTES, Herpes Simplex Virus-thymidine kinase (HSV-tk), cytosine deaminase, and caspase-3.

In still other embodiments of the invention, the ICP10 polynucleotide is modified by insertion of a polynucleotide encoding a reporter protein. Exemplary non-limiting polynucleotides encoding for reporter proteins include green fluorescent protein, enhanced green fluorescent protein, β-galactosidase, luciferase, and HSV-tk.

C. Ribonucleotide Reductase Activity Assay

The biologic activity of RR can be detected as previously described (Averett, et al., *J. Biol. Chem.* 258:9831-9838 (1983) and Smith et al., *J. Virol.* 72:9131-9141 (1998)) with the following modifications. BHK cells are initially grown to confluence in complete GMEM (containing 10% FBS) and then incubated for three days in 0.5% FBS EMEM, followed by infection with 20 pfu of wild-type HSV, HSV-2 mutant, or mock infection. The cells are harvested 20 hours post infection, resuspended in 500 μl HD buffer [100 mM HEPES buffer (pH 7.6), 2 mM dithiothreitol (DTT)] and incubated on ice for 15 minutes before a 30 second sonication. Cell debris is cleared by centrifugation (16,000 g, 20 minutes, 4° C.) and the supernatant is precipitated with crystalline ammonium sulfate at 45% saturation (0.258 g/ml). After a second centrifugation (16,000 g, 30 minutes), the pellets are dissolved in 100 μl HD buffer, from which 50 μl is taken to mix with an equal volume of 2× reaction buffer (400 mM HEPES buffer (pH 8.0), 20 mM DTT and 0.02 mM [$^3$H]-CDP (24 Ci/mmol, Amersham, Chicago, Ill.). The reaction is terminated by the addition of 100 mM hydroxyurea with 10 mM EDTA (pH 8.0) and boiling for 3 minutes. Then 1 ml of *Crotalux atrox* venom (Sigma, St. Louis, Mo.) is added and incubated for 30 minutes at 37° C., followed by another 3 minute boiling. The solution is then passed through a 0.5 ml Dowex-1 borate column, and samples eluted with 2 ml water and collected in four elution fractions for scintillation counting after mixing with Biofluor (New England Nuclear, Boston, Mass.). Ribonucleotide reductase activity is expressed as units/mg protein where 1 unit represents the conversion of 1 nmol [$^3$H]CDP to dCDP/hr/mg protein.

D. Protein Kinase Activity Assay

To determine whether the modified ICP10 polynucleotide encodes a polypeptide that lacks protein kinase activity, extracts of cells infected with HSV-2 having a modified ICP10 polynucleotide or wild-type HSV-2 (moi=200, 16 hours post infection) are immunopercipitated with anti LA-1 antibody and subjected to PK assays as described in Chung et al. *J. Virol.* 63:3389-3398, 1998 and U.S. Pat. No. 6,013,265. Generally, immunopercipitates of cell extracts are normalized for protein concentration using a BCA protein assay kit (PIERCE, Rockford Ill.) washed with TS buffer containing 20 mM Tris-HCL (pH 7.4), 0.15 M NaCl, suspended in 50 μl kinase reaction buffer consisting of 20 mM Tris-HCL (pH 7.4) 5 mM $MgCl_2$, 2 mM Mn $Cl_2$, 10 μCi [$^{32}$p] ATP (3000 Ci/mmol, DuPont, New England Research Prod.) and incubated at 30° C. for 15 minutes. The beads are washed once with 1 ml TS buffer, resuspended in 100 μl denaturing solution and boiled for 5 minutes. Proteins are then resolved by SDS-PAGE on a 7% polyacrylamide gel. Proteins are then electrotransferred onto nitrocellulose membranes as previously described (see, Aurelian et. al., *Cancer Cells* 7:187-191 1989) and immunoblotted by incubation with specific antibodies followed by protein A-peroxidase (Sigma, St. Louis, Mo.) for 1 hour at room temperature. Detection can be made with ECL reagents (Amersham, Chicago, Ill.) as described in Smith et al., *Virol.* 200:598-612, (1994).

IV. Vector Construction

The present invention is directed to an HSV-2 vector comprising a replacement or deletion of at least part of an ICP10 sequence, such that the protein encoded for by the modified ICP10 polynucleotide has ribonucleotide reductase activity, but lacks protein kinase activity, and in specific embodiments further comprising a regulatory sequence, such as a constitutive promoter. In some embodiments, the composition is a naked (non-viral) DNA vector comprising the modified ICP10 gene, and in other embodiments, the composition is a recombinant HSV-2 having the modified ICP10 gene. Both the naked DNA vector, and the recombinant virus can be further comprised of some or all of the following components.

A. Vectors

Vectors, as defined supra, include but are not limited to plasmids, cosmids, viruses (bacteriophage, animal viruses, and plant viruses), and artificial chromosomes (e.g., YACs). Methods for the construction of engineered viruses and DNA vectors are known in the art. Generally these include Sambrook et al., *Molecular Cloning: A Laboratory Manual,* 2nd Ed., Cold Spring Harbor Laboratory Press (1989) and the references cited therein. Virological considerations are also reviewed in Coen D. M, *Molecular Genetics of Animal Viruses in Virology,* 2.sup.nd Edition, B. N. Fields (editor), Raven Press, N.Y. (1990) and the references cited therein.

Expression vectors can contain a variety of "control sequences," which refer to nucleic acid sequences necessary for the transcription and possibly translation of an operably linked coding sequence in a particular host cell. In addition to control sequences that govern transcription and translation, DNA vectors, expression vectors, and viruses may contain nucleic acid sequences that serve other functions as well and are described infra.

1. Promoters and Enhancers

A promoter generally comprises a sequence that functions to position the start site for RNA synthesis. The best-known example of this is the TATA box, but in some promoters lacking a TATA box (e.g., the promoter for the mammalian terminal deoxynucleotidyl transferase gene and the promoter for the SV40 late genes) a discrete element overlying the start site itself helps to fix the place of initiation. Additional promoter elements regulate the frequency of transcriptional initiation. Typically, these are located in the region 30 to 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an enhancer.

A promoter may be one naturally associated with a nucleic acid sequence, as may be obtained by isolating the 5' non-coding sequences located upstream of the coding segment and/or exon. Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the 0 lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR, in connection with the compositions disclosed herein (see U.S. Pat. Nos. 4,683,202 and 5,928,906). Furthermore, it is contemplated that control sequences, which direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination may be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art. Non-limiting examples of such regions include the human LIMK2 gene (Nomoto et al. (1999) *Gene* 236(2):259-271), the somatostatin receptor-2 gene (Kraus et al., (1998) *FEBS Lett.* 428(3): 165-170), murine epididymal retinoic acid-binding gene (Lareyre et al., (1999) *J. Biol. Chem.* 274(12):8282-8290), human CD4 (Zhao-Emonet et al., (1998) *Biochem. Biophys. Acta,* 1442 (2-3):109-119), mouse α-2 (XI) collagen (Tsumaki, et al., (1998), *J. Biol. Chem.* 273(36):22861-4) INA dopamine receptor gene (Lee, et al., (1997), *DNA Cell Biol.* 16(11): 1267-1275) insulin-like growth factor II (Vu et al., (1997) *Biophys Biochem Res. Comm.* 233(1):221-226) and human platelet endothelial cell adhesion molecule-1 (Almendro et al., (1996) *J. Immunol.* 157(12):5411-5421).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819).

3. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to be more stable and are translated more efficiently. Thus, in other embodiments involving eukaryotes, it is contemplated that the terminator comprise a signal for the cleavage of the RNA, and that the terminator signal promote polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

4. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, both of which are convenient and known to function well in various target cells. Polyadenylation may increase the stability of the transcript or may facilitate cytoplasmic transport.

5. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with fluorescence activated cell sorting (FACS) analysis. The marker used is not believed to be important, so long as it is capable of being expressed simultaneously with the nucleic acid encoding a gene product. Further examples of selectable and screenable markers are well known to one of skill in the art.

The vector is introduced to the initially infected cell by suitable methods. Such methods for nucleic acid delivery for transformation of an organelle, a cell, a tissue or an organism for use with the current invention are believed to include virtually any method by which a nucleic acid (e.g., HSV vector) can be introduced into an organelle, a cell, a tissue or an organism, as described herein or as would be known to one of ordinary skill in the art. Non-limiting exemplary methods include: direct delivery of DNA by ex vivo transfection; injection (U.S. Pat. Nos. 5,994,624, 5,981,274, 5,945,100, 5,780,448, 5,736,524, 5,702,932, 5,656,610, 5,589,466 and 5,580,859); microinjection (U.S. Pat. No. 5,789,215); electroporation (U.S. Pat. No. 5,384,253); calcium phosphate precipitation; DEAE dextran followed by polyethylene glycol; direct sonic loading; liposome mediated transfection; receptor-mediated transfection; microprojectile bombardment (PCT Application Nos. WO 94/09699 and 95/06128; U.S. Pat. Nos. 5,610,042; 5,322,783 5,563,055, 5,550,318, 5,538,877 and 5,538,880); agitation with silicon carbide fibers (U.S. Pat. Nos. 5,302,523 and 5,464,765); *Agrobacterium* mediated transformation (U.S. Pat. Nos. 5,591,616 and 5,563,055); PEG mediated transformation of protoplasts (U.S. Pat. Nos. 4,684,611 and 4,952,500); desiccation/inhibition mediated DNA uptake, and any combination of these methods, or other methods known to persons of skill in the art. The composition can also be delivered to a cell in a mammal by administering it systemically, such as intravenously, in a pharmaceutically acceptable excipient.

B. Methods of DNA Vector Delivery to Cells

1. Ex Vivo Transformation

Methods for transfecting cells and tissues removed from an organism in an ex vivo setting are known to those of skill in the art. Thus, it is contemplated in the present invention that cells or tissues may be removed and transfected ex vivo using the nucleic acids and compositions described herein. In particular aspects, the transplanted cells or tissues may be placed into an organism. In some embodiments, a nucleic acid is expressed in the transplanted cell or tissue.

2. Injection

In certain embodiments, a nucleic acid may be delivered to an organelle, a cell, a tissue or an organism via one or more injections (i.e., a needle injection), such as, for example, subcutaneously, intradermally, intramuscularly, intravenously, intraperitoneally, etc. Methods of injection are well known to those of ordinary skill in the art (e.g., injection of a composition comprising a saline solution). Further embodiments of the present invention include the introduction of a nucleic acid by direct microinjection. The amount of composition of the present invention used may vary upon the nature of the cell, tissue or organism affected.

3. Electroporation

In certain embodiments of the present invention, a nucleic acid is introduced into an organelle, a cell, a tissue or an organism via electroporation. Electroporation involves the exposure of a suspension of cells and DNA to a high voltage electric discharge. In some variants of this method, certain cell wall degrading enzymes, such as pectin degrading enzymes, are employed to render the target recipient cells more susceptible to transformation by electroporation than untreated cells (U.S. Pat. No. 5,384,253). Alternatively, recipient cells can be made more susceptible to transformation by mechanical wounding.

4. Liposome Mediated Transfection

In a further embodiment of the invention, a composition as described herein, such as a vector having a modified ICP10 polynucleotide, may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self rearrangement before the formation of closed structures and entrap water and dissolved solutes between the lipid bilayers. Also contemplated is an nucleic acid complexed with Lipofectamine (Gibco BRL) or Superfect (Qiagen).

In certain embodiments of the invention, a liposome may be complexed with a hemagglutinatin virus (HVJ). This has been shown to facilitate fusion with the cell membrane and promote cell entry of liposome encapsulated DNA (Kaneda et al., (1989) *Science* 20; 243(4889):375-8). In other embodiments, a liposome may be complexed or employed in conjunction with nuclear non histone chromosomal proteins (HMG1) (Kato et al., (1991) *J Biol Chem*. (1991) February 25; 266(6):3361-4). In yet further embodiments, a liposome may be complexed or employed in conjunction with both HVJ and HMG 1. In other embodiments, a delivery vehicle may comprise a ligand and a liposome.

5. Receptor Mediated Transfection

A nucleic acid may be delivered to a target cell via receptor mediated delivery vehicles. This approach takes advantage of the selective uptake of macromolecules by receptor mediated endocytosis. In view of the cell type specific distribution of various receptors, this delivery method adds another degree of specificity to the present invention.

In certain embodiments, the receptor mediated gene targeting vehicle comprises a receptor specific ligand and a nucleic acid binding agent. Other embodiments comprise a receptor specific ligand to which the nucleic acid to be delivered has been operatively attached. Several ligands have been used for receptor mediated gene transfer including the epidermal growth factor (EGF), which has been used to deliver genes to squamous carcinoma cells as described in European Patent No. EPO 0 273 085.

In other embodiments, a nucleic acid delivery vehicle component of a cell specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell.

In still further embodiments, the nucleic acid delivery vehicle component of a targeted delivery vehicle may be a liposome itself, which will preferably comprise one or more lipids or glycoproteins that direct cell specific binding. For example, lactosyl ceramide, a galactose terminal asialganglioside, has been incorporated into liposomes and an increase in the uptake of the insulin gene by hepatocytes has been observed (Nicolau et al., (1987) *Methods Enzymol.* 149:157-76). It is contemplated that the tissue specific transforming constructs of the present invention can be specifically delivered into a target cell in a similar manner.

6. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application No. WO 94/09699). This method depends on the ability to accelerate microprojectiles that are either coated with DNA or contain DNA, to a high velocity allowing them to pierce cell membranes and enter cells without killing them. The microprojectiles may be comprised of any biologically inert substance, such as tungsten, platinum, or gold. For the bombardment, cells in suspension are concentrated on filters or solid culture medium. Alternatively, immature embryos or other target cells may be arranged on solid culture medium. The cells to be bombarded are positioned at an appropriate distance below the microprojectile bombardment device on a stopping plate. A wide variety of microprojectile bombardment techniques useful for practice with the current invention will be known to persons of skill in the art.

C. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells that do not contain a recombinantly introduced nucleic acid.

A tissue may comprise a host cell or cells to be transformed with a cell membrane fusion-generating HSV-2 mutant. The tissue may be part or separated from an organism. In certain embodiments, a tissue may comprise, but is not limited to, adipocytes, alveolar, ameloblasts, neural, basal cells, blood (e.g., lymphocytes), blood vessel, bone, bone marrow, glial cell, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, small intestine, spleen, stem cell, stomach, testes, and all cancers thereof.

In certain embodiments, the host cell or tissue may be comprised in at least one organism. In certain embodiments, the organism may be, but is not limited to, a prokaryote (e.g., a eubacteria, an archaea) or a eukaryote, as would be understood by one of ordinary skill in the art.

Numerous cell lines and cultures are available for use as a host cell, and are commercially available through organizations such as the American Type Culture Collection (ATCC). An appropriate host can be determined by one of skill in the art based on the vector backbone and the desired result. Exemplary non-limiting cell types available for vector replication and/or expression include bacteria, such as *E. coli* (e.g., *E. coli* strains RR1, LE392, B, X 1776 (ATCC No. 31537), W3110, F, lambda, DH5α, JM109, and KC8); bacilli e.g., *Bacillus subtilis*; other enterobacteriaceae e.g., *Salmonella typhimurium, Serratia marcescens*, as well as a number of commercially available bacterial hosts and competent cells such as SURE® Competent Cells and SOLOPACK™ Gold Cells (STRATAGENE®, La Jolla, Calif.). Non-limiting examples of eukaryotic host cells for replication and/or expression of a vector include, HeLa, NIH3T3, Jurkat, 293, Cos, CHO, Saos, and PC12.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

D. Viral Vector Packaging and Propagation

1. Viral Packaging

In specific embodiments of the present invention, after the ICP10 gene has been modified, it is inserted into the virus through homologous recombination. Typically, this is done by co-transfecting the plasmid DNA containing the modified ICP10 gene with purified HSV-2 genomic DNA into Vero cells using Lipofectamine. The recombinant virus is then identified (typically by screening the virus plaques for the presence of a selectable marker) and selecting plaques containing the modified ICP10 polynucleotide. The selected recombinant virus is then characterized in vitro to confirm that the modified ICP10 gene has been correctly inserted into the HSV-2 genome to replace the original ICP10 gene. Viral packaging and in vitro characterization are described in more detail in Examples 1 and 2.

2. Preparation of Viral Stocks

Once the recombinant HSV-2 mutant virus has been selected, viral stocks are prepared as follows. Vero cells are grown in 10% fetal bovine serum (FBS) and infected with 0.01 plaque forming units (pfu) per cell. Viruses are then harvested from the cells 2 days later by repeated freezing and thawing and sonication. The harvested virus is then purified as described (Nakamori, et al., (2003) *Clinical*

*Cancer Res.* 9(7):2727-2733). The purified virus is then titered (as described in Example 10), aliquoted and stored at −80° C. until use.

E. Protein Expression Systems

Protein expression systems may be utilized in the generation of DNA vector compositions of the present invention for example, to express the polypeptide encoded by the modified ICP10 polynucleotide for functional studies. Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236 and is commercially available (e.g., CLONTECH, Inc. Mountain View, Calif.).

Other examples of commercially available expression systems include an inducible mammalian expression system, which involves a synthetic ecdysone-inducible receptor, or a pET expression system, or an *E. coli* expression system (STRATAGENE, LaJolla, Calif.); A tetracycline-regulated expression system, an inducible mammalian expression system that uses the full-length CMV promoter or a yeast expression system designed for high-level production of recombinant proteins in the methylotrophic yeast *Pichia methanolica* (INVITROGEN, Carlsbad, Calif.).

It is contemplated that the proteins, polypeptides or peptides produced by the methods of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analysis, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

V. Functional Roles of a HSV-2 Mutant

A HSV-2 mutant as described herein displays multiple functional roles as an oncolytic agent. For example, the virus can destroy tumor cells by lysis, as well as by syncytial formation, and induction of apoptosis in both infected cells as well as by-stander cells. Furthermore, tumor destruction by the HSV-2 mutant induces a potent anti-tumor immune response that further contributes to the therapeutic efficacy of the mutant virus as an oncolytic agent for the treatment of malignant disease.

The HSV-2 mutant virus displays selective replication in cycling, but not non-cycling cells. As described in more detail in Example 4, the mutant HSV-2, lacking protein kinase activity, shows at least a 40-fold decrease in growth in non-cycling cells as compared to growth in cycling cells. In contrast, the wild-type HSV-2 is only marginally affected in its growth characteristics between cycling and non-cycling cells. Therefore, the HSV-2 mutant as described herein is well suited for use as an oncolytic agent in cycling cells having an activated Ras pathway, such as tumor cells.

The modified HSV-2 described herein has superior tumor cell killing ability compared to other oncolytic viruses and the wild-type HSV-2. Using an in vitro assay as described in Example 5, demonstrates that the killing ability of FusOn-H2 against human tumor cells of different tissue origins is significantly stronger than that of the oncolytic HSV-1 described in U.S. patent application Ser. No. 10/397,635 and/or tested until today, and even exceeds that of the parental wild-type HSV-2. Furthermore, as described in the Example 6, a single injection of the virus of the present invention at a moderate dose ($1\times10^6$ plaque-forming-unit) led to the complete disappearance of breast tumor orthotopically established in nude mice in 100% of the animals (n=8), while administration of the same dose of oncolytic HSV-1 only shrank the tumor in less than 30% of the mice.

In addition to the lytic and fusogenic activities, the HSV-2 mutant also has potent apoptotic inducing activity and is capable of inducing a potent anti-tumor immune response. In an in vitro setting, the HSV-2 mutant can induce apoptosis in cells infected with the virus as well as non-infected by-stander cells that surround the infected cells. Furthermore, HSV-2 mutant is effective at inducing apoptosis of tumor cells in vivo. This is described in greater detail in Example 8. Not only are the compositions described herein more effective at killing tumor cells than other oncolytic viruses, the HSV-2 mutant displays a strong therapeutic effect against primary and metastatic tumor in vivo by induction of a strong anti-tumor immune response. As described in Example 9, the adoptive transferred CTL from FusOn-H2 treated mice can inhibit the growth of the original tumor and effectively prevent the metastases developing.

Apoptosis, or programmed cell death, is an essential process for normal embryonic development, maintaining homeostasis in adult tissues, and suppressing carcinogenesis. In some embodiments of the invention, the modified HSV-2 is a potent inducer of apoptosis in tumor cells infected with the virus, and in non-infected by-stander tumor cells. For example, in a particular embodiment tumor cells were infected with an HSV-2 construct in which parts of the protein kinase domain of the ICP10 gene was replaced with a gene encoding the green fluorescent protein (GFP). Infected cells could be identified under a fluorescent microscope by visualizing the GFP, and cells undergoing apoptosis were identified as evidenced by their chromatin condensation. The ratio of cells showing chromatin condensation to GFP expression was 2.6:1, suggesting that there was a substantial number of tumor cells undergoing apoptosis, that were not infected with the modified HSV-2. The ability of the oncolytic virus of the present invention to induce apoptosis is described in more detail in Example 8.

Strong anti-tumor immune responses are useful in combating malignant disease. The HSV-2 mutant described herein is capable of inducing a potent antitumor immune response against primary and metastatic tumors in vivo. In a particular embodiment, the mutant HSV-2 (FusOn-H2) selectively replicated in and lysed tumor cells in a mouse mammary tumor model using the 4T1 mouse mammary tumor cell line, and showed a strong therapeutic effect against primary and metastatic tumor in vivo by induction of strong antitumor immune response. Specifically, adoptive transferred cytotoxic T lymphocytes (CTL) from FusOn-H2 treated mice can inhibit growth of the original tumor and effectively prevent metastasis in mice not treated with FusOn-H2. This is described in more detail in Example 9.

VI. Pharmaceutical Compositions and Routes of Administration

A. General Considerations

Compositions of the present invention can be administered as a pharmaceutical composition comprising either a recombinant HSV-2 mutant having a modified ICP10 gene, or as a naked (non-viral) DNA vector having a modified ICP10 gene, as described herein. The compositions of the present invention include classic pharmaceutical preparations. In general, the compositions of the present invention can be administered as pharmacological agents by dissolving or dispersing the composition in a pharmaceutically acceptable carrier or aqueous medium. The use of such media and agents for pharmaceutical active substances is well known in the art. Except insofar as any conventional media or agent is incompatible with the compositions of the invention, its use in a therapeutic composition is contemplated. Supplementary active ingredients, such as other anti-disease agents, can also be incorporated into the pharmaceutical composition. Administration of the composition will be via any common route so long as the target cell is available via that route. Exemplary administration routes include oral, nasal, buccal, rectal, vaginal or topical. Alternatively, administration may be by orthotopic, intradermal, subcutaneous, intramuscular, intraperitoneal, intravenous, or direct intratumoral injection. The pharmaceutical formulations, dosages and routes of administration for the compositions of the present invention are described infra.

B. Pharmaceutical Formulation of HSV-2 Mutant

The mutant viral composition of the present invention can be prepared as a pharmacologically acceptable formulation. Typically, the mutant virus is mixed with an excipient which is pharmaceutically acceptable and compatible with the virus. Suitable excipients are, for example, water, saline, dextrose, glycerol, ethanol, or the like and combinations thereof. In addition, if desired, the preparation may contain minor amounts of auxiliary substances such as wetting or emulsifying agents, pH-buffering agents, adjuvants or immunopotentiators, which enhance the effectiveness of the viral mutant (See, Remington's Pharmaceutical Sciences, Gennaro, A. R. et al., eds., Mack Publishing Co., pub., 18th ed., 1990). For example, a typical pharmaceutically acceptable carrier for injection purposes may comprise from 50 mg up to about 100 mg of human serum albumin per milliliter of phosphate buffered saline. Additional non-limiting exemplary non-aqueous solvents suitable for use in the formulation of a pharmacologically acceptable composition include propylene glycol, polyethylene glycol, vegetable oil, sesame oil, peanut oil and injectable organic esters such as ethyloleate. Exemplary non-limiting aqueous carriers include water, aqueous solutions, saline solutions, parenteral vehicles such as sodium chloride, Ringer's dextrose, etc. Intravenous vehicles include fluid and nutrient replenishers. Determining the pH and exact concentration of the various components of the pharmaceutical composition is routine and within the knowledge of one of ordinary skill in the art (See Goodman and Gilman's The Pharmacological Basis for Therapeutics, Gilman, A. G. et al., eds., Pergamon Press, pub., 8th ed., 1990).

Sterile injectable solutions are prepared by incorporating the active compounds in the required amount in the appropriate solvent with various other sterile ingredients as required and described above. Generally, dispersions are prepared by incorporating the various sterilized active ingredients into a sterile vehicle which contains the basic dispersion medium and the required other ingredients as described above.

C. Routes and Dosages for Administration of HSV-2 Mutant

The mutant viral composition may be delivered by any route that provides access to the target tissue. Exemplary non-limiting routes of administration may include oral, nasal, buccal, rectal, vaginal topical, or by injection (including orthotopic, intradermal, subcutaneous, intramuscular, intraperitoneal, intravenous, or direct intratumoral injection). Typically, the viral mutant would be prepared as an injectable, either as a liquid solution or a suspension; a solid form suitable for solution in, or suspension in, liquid prior to injection may also be prepared. The preparation also may be emulsified.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermolysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Those of skill in the art will recognize that the best treatment regimens for using a composition of the present invention to provide therapy can be straightforwardly determined. This is not a question of experimentation, but rather one of optimization, which is routinely conducted in the medical arts. For example, in vivo studies in mice provide a starting point from which to begin to optimize the dosage and delivery regimes. The frequency of injection may initially be once a week. However, this frequency might be optimally adjusted from one day to every two weeks to monthly, depending upon the results obtained from the initial clinical trials and the needs of a particular patient. Human dosage amounts can initially be determined by extrapolating from the amount of composition used in mice.

1. Dosages

The amount of viral vector delivered will depend on several factors including number of treatments, subject to be treated, capacity of the subjects immune system to synthesize anti-viral antibodies, the target tissue to be destroyed, and the degree of protection desired. The precise amount of viral composition to be administered depends on the judgment of the practitioner and is peculiar to each individual. However, suitable dosage ranges from $10^5$ plaque forming units (pfu) to $10^{10}$ pfu. In certain embodiments, the dosage of viral DNA may be about $10^5$, $10^6$, $10^7$, $10^8$, $10^9$, up to and including $10^{10}$ pfu.

D. Non-Viral DNA Vector Formulation

In addition to the formulations described above for viral pharmaceutical formulation, the non-viral DNA vector can also be prepared as a sterile powder for the preparation of pharmacologically acceptable sterile solutions. Typical methods for preparation of sterile powder include vacuum-drying and freeze-drying techniques which yield a powder of the active ingredient plus any additional desired ingredient from a previously sterile-filtered solution thereof.

E. Routes and Dosages for Administration of Non-Viral DNA Vector

Several methods for the delivery of non-viral vectors for the transfer of a polynucleotide of the present invention into a mammalian cell is contemplated. These include calcium phosphate precipitation, DEAE-dextran, electroporation, direct microinjection, DNA-loaded liposomes and lipofectamine-DNA complexes, cell sonication, gene bombardment using high velocity microprojectiles, and receptor-mediated transfection as discussed previously. Some of these techniques may be successfully adapted for in vivo or ex vivo use.

In some embodiments of the present invention, the expression vector may simply consist of naked recombinant DNA or plasmids comprising the polynucleotide. Transfer of the construct may be performed by any of the methods mentioned herein which physically or chemically permeabilize the cell membrane. This is particularly applicable for transfer in vitro, but it may be applied to in vivo use as well.

In other embodiments, the delivery vehicle may comprise a ligand and a liposome. For example, Nicolau et al., employed lactosyl-ceramide, a galactose-terminal asialganglioside, incorporated into liposomes and observed an increase in the uptake of the insulin gene by hepatocytes (Nicolau et al., (1987) *Methods Enzymol.* 149:157-76). Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor (as described in European Patent No. EP 0 273 085) and mannose can be used to target the mannose receptor on liver cells.

In certain embodiments, DNA transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissue.

1. Dosages

In certain embodiments it is envisioned that the dosage may vary from between about $10^3$ pfu/kg body weight to about $10^8$ pfu/kg body weight. In certain embodiments, the dosage may be from about $10^3$, $10^4$, $10^5$, $10^6$, $10^7$, up to and including $10^8$ pfu/kg body weight. Of course, this dosage amount may be adjusted upward or downward, as is routinely done in such treatment protocols, depending on the results of the initial clinical trials and the needs of a particular patient.

VII. Combination Treatments

In order to increase the effectiveness of the methods and compositions of the present invention, it may be desirable to combine the methods and compositions disclosed herein with other anti-cancer agents. This process may involve contacting the cancer cell with a composition of the present invention in conjunction with at least one other anti-cancer agent. This may be achieved by contacting the cell with a single composition or pharmacological formulation that includes both agents, or by contacting the cell with two distinct compositions or formulations. Where two distinct formulations are used, the cancer cell may be contacted either by both formulations at the same time, or where one formulation precedes the other (e.g. where a composition of the present invention is administered either preceding or following administration of another anti-cancer agent) or any combination or repetitive cycle thereof. In embodiments where a composition of the present invention and the other agent are administered separately, one would generally ensure that a significant period of time did not expire between the time of each delivery, such that the composition of the present invention and the other agent would still be able to exert an advantageously combined effect on the cancer cell. This time interval between administration of the two formulations may range from minutes to weeks.

Non-limiting examples of anti-cancer agents that may be used in conjunction with the compositions or methods of the present invention may include chemotherapeutic agents (e.g., cisplatin (CDDP), carboplatin, procarbazine, mechlorethamine, cyclophosphamide, camptothecin, ifosfamide, melphalan, chlorambucil, busulfan, nitrosourea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing); radiotherapeutic agents (e.g., γ-rays, X-rays, microwaves and UV-irradiation, and/or the directed delivery of radioisotopes to tumor cells); immunotherapeutic and immunomodulatory agents; gene therapeutic agents; pro-apoptotic agents and other cell cycle regulating agents well known to persons of skill in the art.

Immunotherapy can also be used in conjunction with the compositions and methods described herein as a combination therapy for the treatment of malignant disease. Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells (e.g. cytotoxic T-cells or NK cells) to actually effect cell killing. The antibody also may be conjugated to a drug or toxin (e.g., a chemotherapeutic, radionuclide, ricin A chain, cholera toxin, pertussis toxin, etc.) and serve merely as a targeting agent. In some embodiments, the effector may be a lymphocyte carrying a surface molecule that interacts, either directly or indirectly, with a tumor cell target. In other embodiments, the tumor cell must bear some marker that is amenable to targeting. Non-limiting exemplary tumor markers suitable for targeting may include carcinoembryonic antigen (CEA), prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Gene therapy can also be used in conjunction with the compositions and methods described herein as a combination therapy for the treatment of malignant disease. Gene therapy as a combination treatment relies on the delivery and expression of a therapeutic gene, separate from the mutant HSV-2 described herein. The gene therapy can be administered either before, after, or at the same time as the HSV-2 mutant described herein. Exemplary non-limiting targets of gene therapy include immunomodulatory agents, agents that affect the up regulation of cell surface receptors and GAP junctions, cytostatic and differentiation agents, inhibitors of cell adhesion, or agents that induce or increase the sensitivity of target cells to apoptosis. Exemplary non-limiting immunomodulatory genes that can be used as part of gene therapy in combination with the present invention include tumor necrosis factor; interferon alpha, beta, and gamma; IL-2 and other cytokines; F42K and other cytokine analogs; Or MIP-1, MIP-1 beta, MCP-1, RANTES, and other chemokines.

An exemplary inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the G1. The activity of this enzyme may be to phosphorylate Rb at late G1. The activity of CDK4 is controlled by an activating subunit, D-type cyclin, and by an inhibitory subunit, the p16INK4 that specifically binds to and inhibits CDK4, and thus may regulate Rb phosphorylation. The p16INK4 gene belongs to a newly described class of CDK-inhibitory proteins that also includes p16B, p19, p21WAF1, and p27KIP 1. Homozygous deletions and mutations of the p16INK4 gene are frequent in human tumor cell lines. Since the p16INK4 protein is a CDK4 inhibitor deletion of this gene may increase the activity of CDK4, resulting in hyperphosphorylation of the Rb protein. Other genes that may be employed with gene therapy to inhibit cellular proliferation include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, frns, trk, ret, gsp, hst, abl, E1A, p300, genes involved in angiogenesis (e.g., VEGF, FGF, thrombospondin, BAI-1, GDAIF, or their receptors) and MCC.

It is further contemplated that the up regulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases in intercellular signaling by elevating the number of GAP junctions would increase the anti-hyperproliferative effects on a neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

All patents, patent applications, and other publications cited in this application, including published amino acid or polynucleotide sequences, are incorporated by reference in their entirety for all purposes.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of FusOn-H2

The construction of the exemplary FusOn-H2 is illustrated in FIG. 1. Initially the HSV genome region comprising the ICP10 left-flanking region (equivalent to nucleotide number of HSV-2 genome 85994-86999) was amplified with the following exemplary pair of primers: 5'-TTGGTCTTCACCTACCGACA (SEQ ID NO:1); and 3'-GACGCGATGAACGGAAAC (SEQ ID NO:2). The RR domain and the right-flank region (equivalent to the nucleotide sequence number of HSV-2 genome 88228-89347) were amplified with the following exemplary pair of primers: 5'-ACACGCCCTATCATCTGAGG (SEQ ID NO:13); and 5'-AACATGATGAAGGGGCTTCC (SEQ ID NO:14). These two PCR products were cloned into pNeb 193 through EcoRI-NotI-XbaI ligation to generate pNeb-ICP10-deltaPK. Then, the DNA sequence containing the CMV promoter-EGFP gene was PCR amplified from pSZ-EGFP with the following exemplary pair of primers: 5'-ATGGTGAGCAAGGGCGAG (SEQ ID NO:3); and 3'-CTTGTACAGCTCGTCCATGC (SEQ ID NO:4). The PCR-amplified DNA was then cloned into the deleted PK locus of pNeb-ICP10-deltaPK through BglII and NotI ligation to generate pNeb-PKF-2. During the design of PCR amplification strategies, the primers were designed such that the EGFP gene was fused in frame with the remaining RR domain of the ICP10 gene so that the new protein product of this fusion gene comprises the intact functional EGFP, which would facilitate the selection of the recombinant virus in the following experimental steps.

The modified ICP10 gene was inserted into the virus through homologous recombination by co-transfecting the pNeb-PKF-2 plasmid DNA with purified HSV-2 genomic DNA (strain 186) into Vero cells by lipofectamine. The recombinant virus was screened and identified by selecting GFP-positive virus plaques. During the screening process, it was noticed that all of the GFP-positive plaques showed clear syncytial formation of the infected cells, indicating that this modified virus induces widespread cell membrane fusion, in specific embodiments of the invention. A total of 6 plaques were picked. One of them, referred to as FusOn-H2, was selected for further characterization and for all of the subsequent experiments.

Example 2

In Vitro Characterization

The exemplary FusOn-H2 vector was characterized by standard methods in the art.

Southern Blot Analysis

Figure 2:
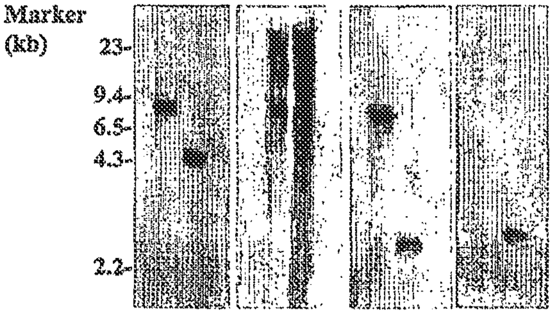
FIG. 2 shows a Southern blot analyses of FusOn-H2. Southern blot hybridization, showing BamHI digested virion DNA from either the parental wild-type HSV-2 (w) or FusOn-H2 (m). The four probes used for the Southern hybridization were: PKL, made from the left-flank; PK, made from the PK domain region; PKR, made from the right-flank region; GFP, prepared from the EGFP gene.
Figure 3:
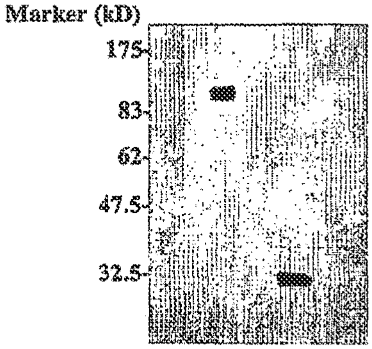
FIG. 3 shows a western blot analysis of FusOn-H2 using an anti-GFP mAb. Cell lysates were prepared from Vero cells infected with either FusOn-H2 (m) or its parental wild-type HSV-2 (w), or from Vero cells transfected with pSZ-EGFP plasmid DNA (p).
Figure 4:
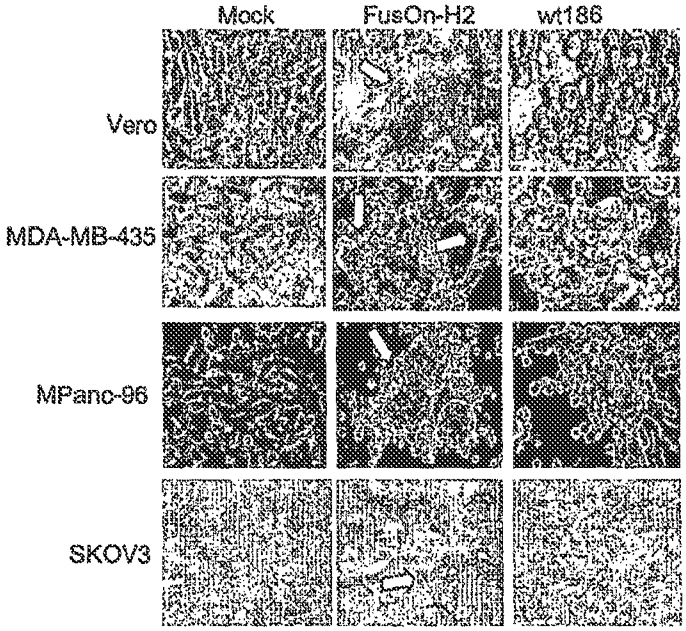
FIG. 4 shows phenotypic characterization of FusOn-H2 in cultured cells. Cells were infected with the indicated viruses at 0.01 pfu/cell or left uninfected. The micrographs were taken 24 h after infection. The syncytia are identified by white arrows. Among the cells tested, MDA-MB-435 is a human breast cancer line, MPans-96 is a human pancreatic cancer line and SKOV3 is a human ovarian cancer line. Original magnification: 200×.

To confirm that the modified ICP10 gene has been correctly inserted into the HSV-2 genome to replace the original ICP10 gene, virion DNA was extracted from purified FusOn-H2 virus stock. As a control, virion DNA from the parental wild type HSV-2 was extracted according to the same procedure. The virion DNA was digested with BamHI and electrophoresed in an 0.8% agarose gel. BamHI digestion generates an 7390 bp DNA fragment from the wild type HSV-2 genome that comprises the entire ICP10 gene and its left and right flank regions. However, digestion of FusOn-H2 genome by the same enzyme generates two DNA fragments from the ICP10 gene locus: 1) a 4830 bp fragment comprising the left-flank and the CMV promoter sequence; and 2) a 3034 bp sequence comprising the GFP, RR, and the right-flank region. The DNA was transferred to a nylon membrane and hybridized with four probes prepared from:

1) the left-flank region of DNA sequence, 2) the whole PK region; 3) the right-flank region of PK; and 4) GFP gene. The result (FIG. 2) showed that all of the probes except the one made from GFP gene hybridized to a 7390 hp DNA band. The left-flank probe hybridized to a DNA band that was identified by the probes prepared from the GFP and the right-flank DNA sequences. The probe made from the PK domain sequence failed to hybridized to either of the DNA fragments, indicating that the PK domain has been completely deleted from the genome of FusOn-H2.

Western Blot Hybridization

To further confirm the correctness of the modified ICP10 gene in the genome of FusOn-H2, proteins were extracted from Vero cells infected with either FusOn-H2 or the parental wild type HSV-2, or from cells transfected with the pSZ-EGFP plasmid DNA. The proteins were separated on a 12% SDS-PAGE gel and transferred to Hybond-C membrane. The membrane was then blotted with an anti-GFP monoclonal antibody (Anti-GFP #Ab290, ABCAM Inc., Cambridge, Mass.). This anti-GFP antibody picked up the smaller GFP protein (around 28 kD) expressed from the pSZ-EGP transfected cells. The same antibody also identified a significantly bigger protein band (the size of the fusion protein is expected to be around 120 kD). However, this antibody failed to react to any protein products from wild type HSV-2 infected cells, confirming the specificity of this antibody. These results further confirm that the GFP gene has been correctly fused with the remaining RR domain of the ICP10 gene in the FusOn-H2 genome.

Example 3

In Vitro Phenotypic Characterization of FusOn-H2

To determine the phenotype of FusOn-H2, the present inventors infected Vero cells with either wild type HSV-2 or FusOn-H2, or the cells were left uninfected. Twenty-four hours after infection, a clear syncytial formation was visible in the cell monolayer infected with FusOn-H2. No syncytium was seen in either uninfected cells or cells infected with the wild type HSV-2. Similar syncytial formation was also observed in human tumor cells of different tissue origin. In some tumor cells, the infection of wild type HSV-2 also induced some syncytial formation. However, the syncytial formation induced by FusOn-H2 on these cells usually was significantly more profound. So in this case, the FusOn-H2 has an enhanced fusogenic activity when compared with the parental wild type HSV-2. These results indicate that FusOn-H2 is phenotypically different from the parental virus in that its infection induces widespread syncytial formation or enhances the intensity of syncytial formation in tumor cells. Neither the PK domain nor the entire ICP10 gene have been previously reported to have any functional link with cell membrane fusion (Smith et al., (1998) *J. Virol.* 72(11):9131-9141; Smith et al., (1994) *Virol* 200(2):598-612; Smith et al., (1992) *J. Gen. Virol.* 73(pt6):1417-1428). In some embodiments, the addition of the GFP gene and/or the replacement of the natural promoter of ICP10 with the strong CMV promoter contributed to this phenotypic change of the virus. The fusogenic phenotype of FusOn-H2 is important for the application of oncolytic purposes, since syncytial formation induced by a type 1 oncolytic HSV was shown to significantly increase the killing ability of the virus against human tumor cells, for example (U.S. patent application Ser. No. 10/397,635, filed Mar. 26, 2003).

Example 4

Growth Curve of FusOn-H2 in Cycling and Non-Cycling Cells

Figure 5A:
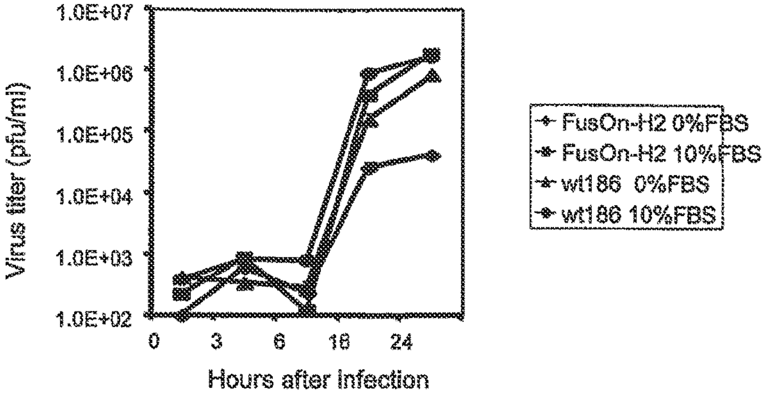
FIGS. 5A, 5B, and 5C shows selective replication of FusOn-H2.
Figure 5B:
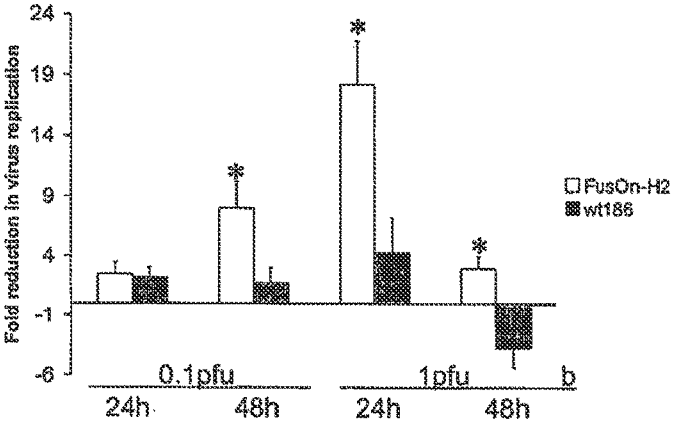
Figure 5C:
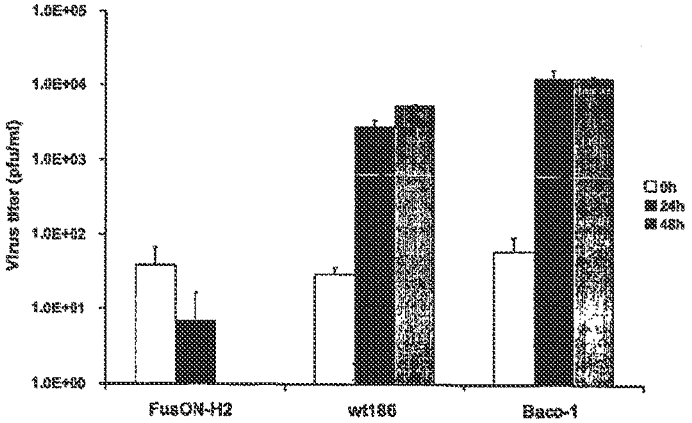

To determine the property of selective replication of FusOn-H2 in dividing (tumor) cells, the inventors infected Vero cells, cultured in medium containing either 10% fetal bovine serum (FBS) (cells therefore in fully cycling) or in medium containing no FBS (cells in non-cycling), with either wild type HSV-2 or FusOn-H2. Virus was harvested at different time points after infection and titrated with Vero cells. The growth of wild type virus was only marginally affected (less than 2-fold) when the cells were put in a non-cycling state. In contrast, the growth of FusOn-H2 in non-cycling cells was dramatically reduced (more than 40-fold) when compared with the virus yield from cells in a cycling state. These results (FIG. 5) indicated that, although fully replication competent in tumor cells, the FusOn-H2 has minimal replication capability in non-cycling cells, which usually represent the normal somatic cells in the body, thus providing for selective replication capability of FusOn-H2 in tumor cells.

Example 5

In Vitro Killing Assay of FusOn-H2 Against Human Tumor Cells

Figure 6A:
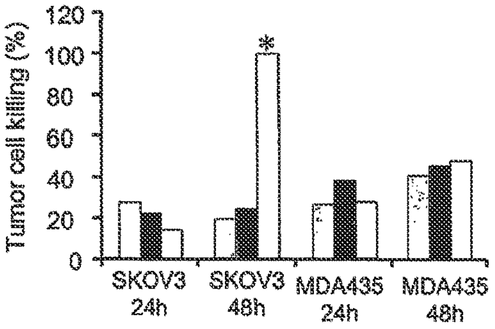
FIGS. 6A and 6B. In vitro killing ability of human cancer cells by oncolytic HSVs. Cells were infected with the viruses at either 0.01 pfu/cell (A) or 0.1 pfu/cell (B). Cell viability was determined with an LDH assay at the indicated times points. The percentage of cell killing was calculated by dividing the LDH released from virus-infected cells by that from uninfected cells; $p<0.01$, FusOn-H2 compared with wt186 or Baco-1; $^{\Psi}p<0.01$, FusOn-H2 compared with wt186 (Student's t-test).
Figure 6B:
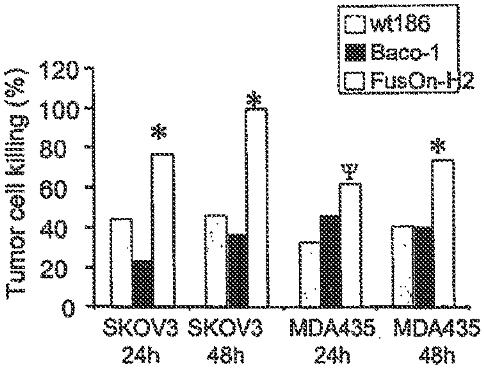

Next, the present inventors directly compared the in vitro oncolytic effect of FusOn-H2 and its parental wild type HSV-2 or an oncolytic virus constructed from the type 1 HSV (HSV-1). Exemplary human ovarian cancer cell line Skov-3 or human breast cancer cell line MDA-MB-435 were infected with the viruses at either 0.01 or 0.1 pfu/cell, and the cell viabilities were determined by calorimetric lactate dehydrogenase (LDH) assay, for example, at either 24 or 48 h after virus infection. The result (FIG. 6) demonstrates that, among the oncolytic HSVs tested, the FusOn-H2 has the highest killing ability against both human tumor cell lines. Its killing ability was even significantly higher than that from its parental wild-type virus due to its ability to induce syncytial formation in the tumor cells.

Example 6

In Vivo Therapeutic Evaluation of FusOn-H2

The exemplary FusOn-H2 virus was characterized under in vivo conditions.

Against Human Breast Cancer Xenografts

Figure 7A:
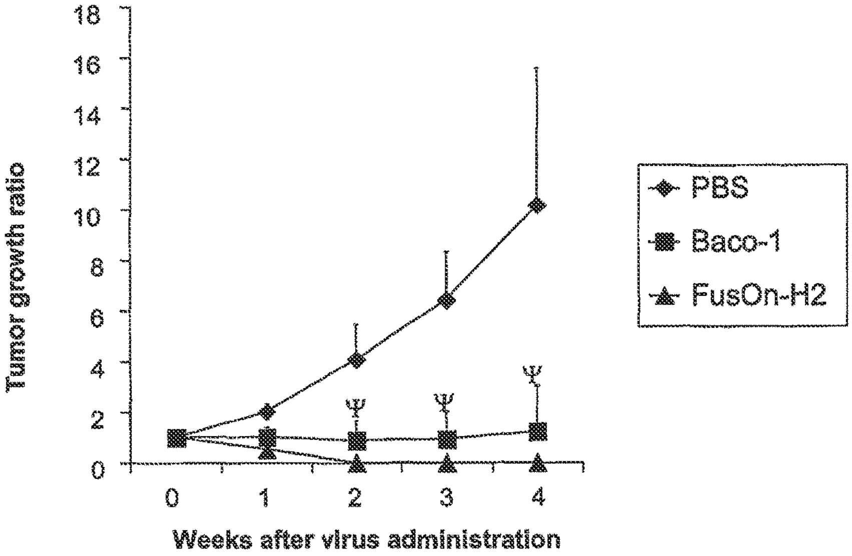
FIGS. 7A and 7B. In vivo anti-tumor activity of FusOn-H2 against xenografted human breast cancer.
Figure 7B:
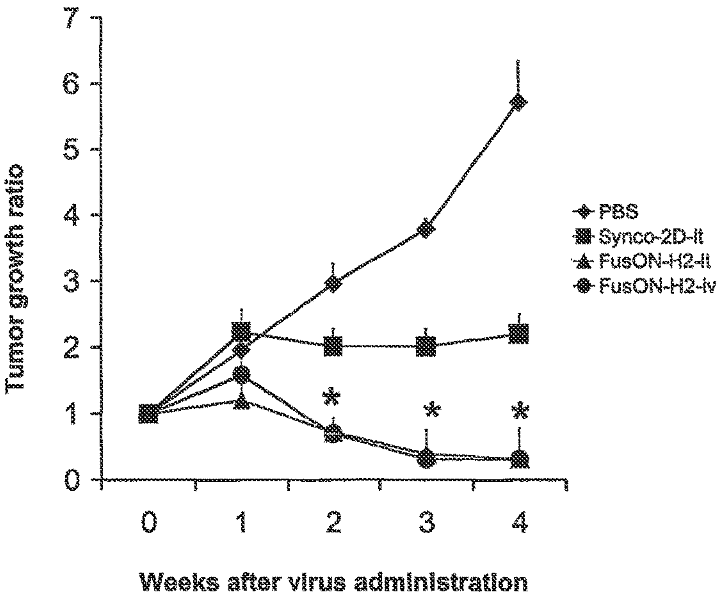

To evaluate the anti-tumor effect of FusOn-H2 in vivo, the present inventors injected the virus at a very moderate dose ($1\times10^6$ pfu) directly into established xenografts (around 5-8 mm in diameter) of human breast cancer (from implantation of MDA-MB-435 cells in the mammary fat pad). For comparison purposes, the present inventors included an oncolytic HSV derived from HSV-1 (Baco-1), that was used at the same dose as FusOn-H2; Baco-1 is described in U.S. patent application Ser. No. 10/397,635, filed Mar. 26, 2003. Tumor sizes were measured weekly for 4 weeks. As compared with the PBS controls, a single injection of either viruses had an immediate effect on tumor growth (FIG. 7). Within 1 week of virus injection, the tumors in mice treated with either of the oncolytic viruses were significantly smaller than tumors injected with PBS ($P<0.001$). From week 2 to week 4, however, FusOn-H2 produced significantly greater anti-tumor effects than did Baco-1 ($P<0.01$). All of the animals (8 of 8) were tumor-free by week 2 after FusOn-H2 administration. By contrast, only 2 mice in the group injected with Baco-1 were tumor-free. In the other 6 mice, tumors that had shrunk initially began to re-grow by week 3 after virus injection. These results indicate that FusOn-H2 is a potent anti-tumor agent against human breast cancer and is significantly more effective than the fusogenic oncolytic HSV constructed from HSV-1.

Against Human Ovarian Cancer Xenografts

Figure 8:
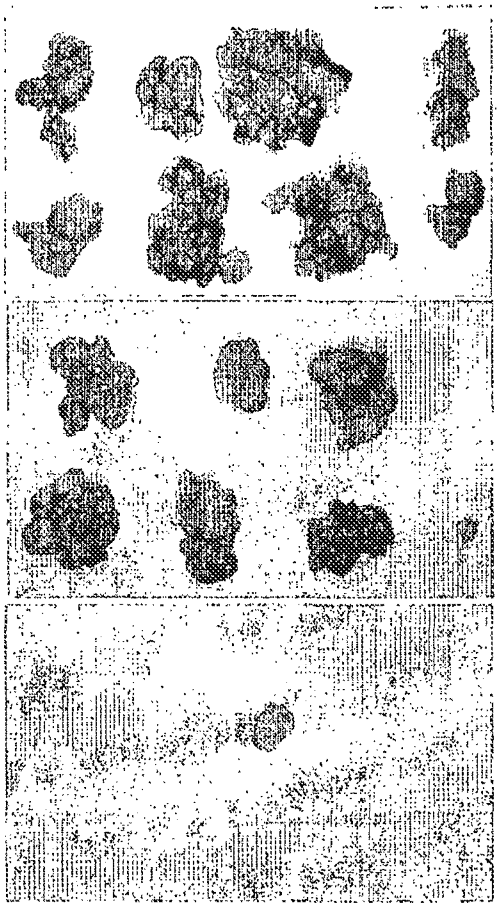
FIG. 8. Therapeutic effect of FusOn-H2 against metastatic human ovarian cancer xenografts established in the peritoneal cavity of nude mice. Human ovarian cancer xenografts were established by intraperitoneal inoculation of $2\times10^6$ SKOV3 cells into the peritoneal cavity (n=8 mice per treatment group). Eight and 15 days after tumor cell inoculation, the mice received an intraperitoneal injection of oncolytic HSVs at a dose of $3\times10^6$ pfu, at a site distant from the tumor implantation site. Four weeks after the initial virus injection (i.e., 5 weeks after tumor cell implantation), the mice were euthanized. The gross appearance of the tumor nodules is shown in this figure while the number of tumor nodules and the tumor weight from each animal are shown in Table 1.

Peritoneal invasion of ovarian cancer is a common and serious clinical problem. It has been reported that about 70% of late-stage ovarian cancer patients have metastatic disease in the peritoneal cavity. The present inventors therefore chose a peritoneal metastasis model (xenografted Skov-3 cells) as a means to test the efficacy of FusOn-H2 against human ovarian cancer, for example. Freshly harvested Skov-3 cells were inoculated into the peritoneal cavities of nude mice at a dose of $3\times10^6$ cells/mouse. Two weeks later, mice received a single intraperitoneal (i.p.) injection with $3\times10^6$ pfu of either Baco-1, FusOn-H2, or PBS (control) at a site distant from that of tumor cell implantation. This therapeutic injection was repeated one week later. Four weeks after the initial therapeutic injection, mice were euthanized and the tumor growth in the abdomen cavity was evaluated. There was a clear i.p. dissemination of tumor in either PBS- or Baco-1-treated group, as indicated by the revelation of multiple tumor nodules across the cavity in each animal of these treatment groups (FIG. 8 and Table 1).

TABLE 1

Number and weight of tumor modules in the abdominal cavity after oncolytic treatment of human ovarian cancer xenografts

| | PBS | | Baco-1 | | FusOn-H2 | |
|---|---|---|---|---|---|---|
| Treatments Mouse no. | Tumor nodules | Tumor weight (g) | Tumor modules | Tumor weight (g) | Tumor modules | Tumor weight (g) |
| 1 | 8 | 0.81 | 5 | 0.93 | 1 | 0.15 |
| 2 | 12 | 0.93 | 1 | 0.02 | 0 | 0 |
| 3 | 9 | 0.65 | 12 | 1.07 | 0 | 0 |
| 4 | 14 | 1 | 0 | 0 | 0 | 0 |
| 5 | 7 | 0.48 | 15 | 1.35 | 0 | 0 |
| 6 | 30 | 1.7 | 2 | 0.63 | 0 | 0 |
| 7 | 19 | 2.29 | 9 | 0.98 | 0 | 0 |
| 8 | 25 | 1.74 | 4 | 0.93 | 0 | 0 |
| mean | 15.5 | 1.2 | 6 | 0.72 | 0.12 | 0.018 |
| SD | 8.4 | 0.6 | 5.4 | 0.4 | 0.35 | 0.05 |

As compared with PBS, Baco-1 treatment provided a certain therapeutic effect against the established ovarian cancer; one mouse was totally tumor-free and one had significantly-reduced tumor nodule (only one tumor nodule was found). The therapeutic effect, however, of FusOn-H2 was clearly more profound. Seven of the eight mice in FusOn-H2-treated group were entirely tumor free by the end of the experiment (Table 1 and FIG. 8). The only mouse that was not tumor-free bore a single tumor nodule that was much smaller than those in Baco-1- or PBS-treated mice. These results clearly demonstrate that FusOn-H2 is also extremely effective at treating human solid tumors established in a relatively large cavity and even when the virus was administered at a very moderate dose.

Example 7

In Vivo Toxicity Evaluation of FusOn-H2

As a first step toward evaluating the toxicity of FusOn-H2, the present inventors injected either wild type HSV-1, HSV-2 or FusOn-H2 at $5\times10^6$ pfu subcutaneously into C57/black mice (N=5). At five days after virus administration, four out of five mice died in the group receiving wild type HSV-1. One mouse from the group receiving wild type HSV-2 died. However, none of the mice died in the group injected with FusOn-H2. These results indicate that although extremely potent at killing tumor cells, FusOn-H2 was significantly less toxic than the parental wild type HSVs to the receiving hosts, and in specific embodiments was safe for clinical application.

Example 8

Ability of FusOn-H2 to Induce Apoptosis

The present example shows that the modified HSV-2 virus (FusOn-H2), as described in the present invention, can efficiently induce apoptosis in infected and by-stander tumor cells, providing an additional tumor destroying mechanism.

African green monkey kidney (Vero) cells, SW403 and SW480 cells (human colon cancer cell lines), and A549 cells (a human lung carcinoma cell line) were obtained from the American Type Culture Collection (Rockville, Md.). EC9706, a human esophageal cancer cell line was provided by Dr. Mingrong Wang (Chinese Academy of Medical Sciences). SKOV3 cells, a human ovarian cancer cell line, was provided by Dr. Robert Bast (the M. D. Anderson Cancer Center). U20S cells, a human osteosarcoma line, was provided by Dr. Lawrence Donehower. All of the cells were cultured in DMEM containing 10% fetal bovine serum (FBS).

FusOn-H2 was derived from the wild-type HSV-2 strain 186 (wt186) and its construction is described in Example 1. The construction of Baco-1, an HSV-1-based oncolytic virus is described in U.S. patent application Ser. No. 10/397,635. Viral stocks were prepared by infecting Vero cells with 0.01 plaque-forming units (pfu) per cell. Viruses were harvested 2 days later and purified as described (Nakamori et al., (2003) *Clinical Cancer Res.* 9(7): 2727-2733). The purified viruses were titrated, aliquoted and stored at −80° C. until use.

Vital Growth Characterization

Cells were seeded in triplicate into 24-well plates at 50% density. Next day, cells were infected with the viruses at 1 pfu/cell for 1 h. Cells were washed once with PBS to remove unabsorbed and uninternalized viruses before fresh medium was added. Cells were harvested at 24 h after infection. Viruses were released by repeated freezing and thawing and sonication. Virus titers were determined on Vero cells by a plaque assay.

Hochest Dye Staining of Infected Cells and Quantification of Chromatin Condensation Cells seeded in 24 well plates were infected next day with FusOn-H2, wt186 or Baco-1 at 10 pfu/cell or mock-infected. Twenty-four h after infection, the cells were stained with Hochest dye 33358 (Sigma-Aldrich, Mo.) at a final concentration of 1 μg/ml for 30 min at 37° C. before photomicrographs were taken under a fluorescent microscope.

DNA Laddering Assay

Cells were seeded into 6-well plates at 70% density. Next day, cells were infected with virus at 10 pfu/cell. Twenty-four h after virus infection, cells were harvested and DNA was extracted from the cells with DNAzol reagent (Invitrogen, Calif.). The extracted DNA was treated with RNase (100 μg/ml) before subjecting to phenol:chloroform extraction and ethanol precipitation. DNA was then loaded to 1% agarose gels for electrophoreses and visualization under UV illumination after staining with ethidium bromide.

Expression of EGFP Corresponds to Chromatin Condensation

Cells seeded in 12 well plates were infected next day with FusOn-H2 at 1 pfu/cell. Hochest dye staining for chromatin condensation was done as described above. The overlay of micrographs from the same field with different fluorescent lights were done by using Spot Image Software (Diagnostic Instrument, Inc, Ill.). The GFP positive and GFP negative apoptotic cells were separately counted in the same fields. About 100 apoptotic cells were counted in each field. A total of 3 fields were calculated for proving the by-stander effect induced by FusOn-H2 infected cells.

Terminal Deoxynucleotidyltransferase-Mediated Nick End Labeling (Tunel) Assay

Female Hsd athymic (nu/nu) mice (obtained from Harlan, Indianapolis, Ind.) were kept under specific pathogen-free conditions and used in experiments when they attained the age of 5 to 6 weeks. EC9706 cells were harvested from subconfluent cultures by a brief exposure to 0.25% trypsin and 0.05% EDTA. After trypsinization was stopped with medium containing 10% FBS, the cells were washed once in serum-free medium and resuspended in PBS. On day 0, $5\times10^6$ EC9706 cells were inoculated into the right flank of nude mice. Two weeks after tumor cell implantation, when the tumors reached approximately 5 mm in diameter, mice received a single intra-tumor injection of $3\times10^6$ pfu of FusOn-H2 or Baco-1 in a volume of 100 μl, or the same volume of PBS. The tumors were measured weekly and their volumes determined by the formula: tumor volume [$mm^3$] =(length [mm])×(width [mm])$^2$×0.52. For Tunel assay, mice were euthanized by $CO_2$ exposure 3 days after intra-tumor injection of $1\times10^7$ pfu of FusOn-H2 or Baco-1 viruses. Tumor tissues were explanted and sectioned for Tunel staining.

FusOn-H2 Induces Apoptosis in Human Tumor Cells of Different Tissue Organs

Due to the anti-apoptotic activity of certain HSV-2 gene products, infection with HSV-2 does not routinely induce apoptosis unless viral protein synthesis is blocked with translation inhibitors such as cycloheximide (Aubert et al., (1999)*J Virol* 73(12): 10359-70). The PK domain of the ICP10 gene from HSV-2 has been identified as one of the viral gene products that have anti-apoptotic function, and its deletion from the viral genome has been described to render the virus with the ability to induce apoptotic death of certain type of somatic cells (Perkins, et al., (2002) *J Virol* 76(3): 1435-49).

To determine if FusOn-H2 induces apoptotic death of tumor cells, we infected a panel of human tumor cells of different tissue origins with the virus at an m.o.i. of 10. An oncolytic virus derived from HSV-1, Baco-1, was included as a control. Among the tumor cells, EC9706 is a human esophagus cancer cell line, SKOV3 is a human ovarian cancer cell line and SW403 and SW480 are human colon cancer cell lines. The cells were seeded in 6-well plates and infected with the viruses the next day. Twenty-four h after infection, the cells were stained with Hochest dye 33358. Infection of tumor cells with FusOn-H2 induced extensive chromatin condensation, indicative of apoptosis. This was evident by the appearance of intense and compact blue nuclear staining in FusOn-H2 infected cells. Overall, over 80% of tumor cells infected with FusOn-H2 showed chromatin condensation. Uninfected tumor cells showed very little or no such apoptotic features. Infection of these tumor cells with either the parental wild type HSV-2 (wt186) or Baco-1 did not significantly increase the background level of blue fluorescent staining for the chromatin condensation.

To further validate the capability of FusOn-H2 to induce apoptosis in tumor cells, DNA fragmentation was analyzed. Three tumor cells that were used in the previous experiment were infected with viruses at 10 pfu/cell or mock-infected. At 24 h post-infection, cells were harvested. DNAs were extracted from the cells and separated in a 1% agarose gel. There was obvious laddering in the wells where FusOn-H2 infected materials were loaded. This laddering was not detected in the wells where DNA sample from either wt186 or Baco-1-infected cells were loaded, thus confirming the result of chromatin condensation presented above. Together, these results demonstrate that infection of FusOn-H2 efficiently induces apoptosis in these human tumor cells, while neither the parental wild type HSV-2 nor an HSV-1-based oncolytic virus has such a property.

Infection of FusOn-H2 Also Induces Apoptotic Death of by-Stander Cells

As FusOn-H2 carries the gene encoding the enhanced green fluorescent protein its infectivity could be easily determined under a fluorescent microscope. During the inter-exchange of fluorescent detection of chromatin condensation and infectivity, we noticed an obvious discrepancy between the percentage of cells showing the blue fluorescent chromatin condensation and the cells showing GFP staining. When the absolute number of tumor cells showing chromatin condensation and GFP expression was enumerated, the ratio was approximately 2.6:1. This result indicates that there was a substantial by-stander apoptotic effect on the surrounding tumor cells of FusOn-H2 infection.

FusOn-H2-Induced Apoptosis Accelerates Tumor Cell Death and Compromises Virus Replication within the Tumor Cells An obvious difference was also noted with regard to the time when cells showed the cytopathic effect (CPE) between the tumor cells infected with FusOn-H2 and the oncolytic virus derived HSV-1. Tumor cells infected with FusOn-H2 at a dose of 1 pfu/cell usually showed full CPE within 24 h, while the tumor cells infected with Baco-1 at the same dose looked largely normal morphologically. They usually did not show obvious sign of CPE until more than 72 h after infection. The typical CPE, including cell round up and detachment from each other, could be readily seen in the wells infected with FusOn-H2 at 24 h after infection, while the cells infected with Baco-1 looked essentially like the mock-infected cells even at 48 h after infection. These results indicate that the apoptotic cell death induced by FusOn-H2 occurred immediately following virus infection, while it took a significantly longer time for the oncolytic effect of virus replication to occur.

Apoptotic Tumor Cell Death is an Important Anti-Tumor Mechanism of the Virus In Vivo The anti-tumor activity of FusOn-H2 in vivo against tumor xenografts established from one of the tumor cells used in the previous experiments was evaluated. Baco-1 was included in this experiment so that the therapeutic effect of these two viruses could be directly compared. Tumor xenografts were established on the right flank though subcutaneous injection of $5\times10^6$ freshly harvested EC9706 cells. When the tumor size reached approximately 5 mm in diameter, mice received a single intra-tumor injection of either viruses (FusOn-H2 or Baco-1) at a dose of $3\times10^6$ pfu, or PBS as a control. The tumors were measured regularly for 6 weeks and the tumor growth ratio was determined by dividing the tumor volume before therapy with those obtained at different time points after therapy. Therapeutic administration of FusOn-H2 essentially stopped the tumor growth within one week. Afterwards the tumor started to shrink and by the end of the experiment, the average tumor size was only about the half of the size before viro-therapy and over half of the mice were completely tumor-free. When compared with the PBS control, administration of Baco-1 did not show any therapeutic effect until week 3. However, it seemed the tumor shrinkage was only transient, as the tumor started to grow again at day 35. Overall, the therapeutic effect of FusOn-H2 was significantly stronger than that of Baco-1 at all of the time points evaluated ($p<0.05$), despite the fact that it has limited replication capability in this tumor cell due induction of apoptosis. These results indicated that the apoptotic death and accompanying bystander effect induced by FusOn-H2 was likely a major anti-tumor mechanism in this in vivo study.

Example 9

Tumor Destruction by FusOn-H2 Induces Potent Antitumor Immunity

The antitumor activity of FusOn-H2 was evaluated in two syngenic tumor models: murine mammary tumor (4T1 cells) and murine neuroblastoma (Neuro2A cells). In both cases, FusOn-H2 produced a statistically significant antitumor effect that was accompanied by robust tumor-specific immune responses. Presented below are typical data from studies in the mammary tumor model.

For this evaluation, 4T1 cells were utilized, which are non-immunogenic, highly malignant and highly metastatic in syngenic BALB/c mice (Aslakson and Miller (1992) *Cancer Res* 52(6): 1399-405; Pulaski and Ostrand-Rosenberg (1998) *Cancer Res.* 58(7): 1486-93). 4T1 cells (105) were orthotopically injected into the mammary fat pad of immune competent BALB/c mice to establish the orthotopic tumor. Mice were left for 10 days, after which lung metastases were detectable in more than 90% of the group. Tumor-bearing mice were then divided into 3 groups (n=10 each) and injected intratumorally with $1\times10^7$ pfu of either FusOn-H2, or other oncolytic HSVs derived from HSV-1, including the doubly fusogenic Synco-2D that was previously shown to induce effective antitumor immunity in this model (Nakamori, Fu et al., (2004) *Mol. Ther.* 9(5): 658-665). Tumor masses at the orthotopic site were measured weekly for 2 weeks, after which the mice were killed for immunological assays and for evaluation of lung metastases (enumerated under a dissecting microscope after Indian ink infusion). For immunological assays, the splenocytes were prepared from the explanted spleens and stimulated with irradiated 4T1 cells in vitro for 5 days before being used for the following assays: 1) tumor-specific CTL activity (with either 4T1 cells or a syngenic sarcoma cell line Meth-A as target cells) by the 51Cr release assay; 2) Elispot analysis of mouse IFN-γ-secreting cells, using a detection kit purchased from BD Biosciences; 3) quantification of cytokine secretion (for both Interferon-γ and IL-10). The results showed that local intratumor administration of FusOn-H2 produced a significantly better therapeutic effect than did other viruses, not just against the orthotopic tumor, but also against distant lung metastases. As compared with Baco-1, Synco-2D was able to inhibit the growth of the orthotopic and metastatic tumors, a result similar to our previous observation (Nakamori, Fu et al., (2004) *Mol. Ther.* 9(5): 658-665). However, FusOn-H2 is apparently even more effective than Synco-2D in treating this tumor. The accompanying antitumor immune responses induced by FusOn-H2, including the tumor-specific CTL activity and frequency and cytokine release, were also more prominent than that of Synco-2D, indicating their contribution to the elimination of local and metastatic tumors.

Example 10

Plaque Forming Assay for Determining Viral Titer

After viral stocks were prepared, the viral titer was determined using a plaque forming assay as previously described (see, Lancz G J. (1974). *Arch Virol.*, 46, 36-43). Vero cells are trypsinized, counted, and plated into six well plates at $4\times10^5$ cells per well and incubated at 37° C. with 5% $CO_2$ and 90% humidity and cultured for 24 hours. Next day, the virus is serially diluted 1:10 in 1× Minimal Essential Medium (MEM) to give six concentrations of $10^{-3}$ to $10^{-8}$. The media is then aspirated from the wells and 0.5 ml of virus dilution is added to each well in triplicate. The plates are then incubated for 1 h with shaking every fifteen min. After the incubation period, the virus solutions are aspirated and 2 mls of MEM containing 1% agarose is added to each well and the plates are incubated for three days, after which the cells are stained with a solution containing 0.1% crystal violet and 20% ethanol. At the end of the 30 minute incubation period, the stain is aspirated, and plaques counted using a stereomicroscope at 10× magnification. Viral titer is then expressed as plaque forming units per ml.

What is claimed is:

1. A composition comprising a fusogenic mutant Herpes Simplex Virus Type 2 (HSV-2) comprising a modified ICP10 coding region lacking nucleotides 1 to 1204 of the endogenous ICP10 coding region, wherein said fusogenic mutant HSV-2 comprises the modified ICP10 operably linked to an endogenous or a constitutive promoter and expresses the modified ICP10 polypeptide that lacks protein kinase (PK) activity but retains ribonucleotide reductase activity; and wherein the fusogenic mutant HSV-2 is capable of selectively killing cancer cells by direct cytolysis and syncytia formation.

2. The composition of claim 1, wherein nucleotides 1 to 1204 of the endogenous ICP10 coding region are replaced by a gene sequence that expresses a fusogenic membrane glycoprotein, wherein the fusogenic membrane glycoprotein is selected from the group consisting of a gibbon ape leukemia virus envelope fusogenic membrane glycoprotein, a C-terminally truncated form of the gibbon ape leukemia virus envelope glycoprotein (GALV.fus), a murine leukemia virus envelope protein, a retroviral envelope protein lacking the cytoplasmic domain, a measles virus fusion protein, a HIV gp 160 protein, an SIV gp160, a retroviral envelope protein, an Ebola virus glycoprotein, and an influenza virus haemagglutinin.

3. The composition of claim 1, wherein nucleotides 1 to 1204 of the endogenous ICP10 coding region are replaced by a gene sequence that expresses a reporter protein, and wherein the gene sequence is selected from the group consisting of sequences that express green fluorescent protein, β-galactosidase, luciferase, and Herpes Simplex Virus thymidine kinase (HSV-tk).

4. The composition of claim 1, wherein nucleotides 1 to 1204 of the endogenous ICP10 coding region are replaced by an immunomodulatory gene, and wherein the immunomodulatory gene is selected from the group consisting of immunomodulatory genes that express tumor necrosis factor, interferon alpha, interferon beta, interferon gamma, interleukin-2, interleukin 12, GM-CSF, F42K, MIP-1, MIP-β, and MCP-1.

5. The composition of claim 1, wherein nucleotides 1 to 1204 of the endogenous ICP10 coding region are replaced by a therapeutic polynucleotide, and wherein the therapeutic polynucleotide is selected from the group consisting of HSVtk, cytosine deaminase, and caspase-3.

6. The composition of claim 1, wherein the constitutive promoter is an immediate early cytomegalovirus promoter.

7. A fusogenic mutant Herpes Simplex Virus Type 2 (HSV-2) comprising a modified ICP10 coding region lacking nucleotides 1 to 1204 of the endogenous ICP10 coding region, wherein said fusogenic mutant HSV-2 comprises the modified ICP10 operably linked to an endogenous or a constitutive promoter and expresses the modified ICP10 polypeptide that lacks protein kinase (PK) activity but retains ribonucleotide reductase activity; and wherein the fusogenic mutant HSV-2 is capable of selectively killing cancer cells by direct cytolysis and syncytia formation.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:synthetic
      amplification primer for left-flanking region of Herpes simplex
      virus-2 (HSV-2) ribonucleotide reductase large subunit (ICP10,
      RR1)

<400> SEQUENCE: 1

ttggtcttca cctaccgaca                                                  20


<210> SEQ ID NO 2
<211> LENGTH: 18
<212> TYPE: DNA
```

<213> ORGANISM: Artificial Sequence
<220> FEATURE:
<223> OTHER INFORMATION: Description of Artificial Sequence:synthetic amplification primer for left-flanking region of Herpes simplex virus-2 (HSV-2) ribonucleotide reductase large subunit (ICP10, RR1)

<400> SEQUENCE: 2
caaaggcaag tagcgcag 18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:synthetic PCR amplification primer for constitutitve immediate early cytomegalovirus (CMV) promoter and enhanced green fluorescent protein (EGFP)

<400> SEQUENCE: 3
atggtgagca agggcgag 18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:synthetic PCR amplificiation primer for constitutive immediate early cytomegalovirus (CMV) promoter and enhanced green fluorescent protein (EGFP)

<400> SEQUENCE: 4
cgtacctgct cgacatgttc 20

<210> SEQ ID NO 5
<211> LENGTH: 120
<212> TYPE: DNA
<213> ORGANISM: Artificial Sequence
<220> FEATURE:
<223> OTHER INFORMATION: Description of Artificial Sequence:C-type retrovirus gibbon ape leukemia virus (GALV) fusogenic membrane envelope glycoprotein (FMG) domain

<400> SEQUENCE: 5
ttaagcctgg taccgtaaca atccctcacc cgttccaggt cggggatcaa gtgcttgtca 60
gacgccatcg acccagcagc cttgagcctc ggtggaaagg cccatacctg gtgttgctga 120

<210> SEQ ID NO 6
<211> LENGTH: 2890
<212> TYPE: DNA
<213> ORGANISM: Artificial Sequence
<220> FEATURE:
<223> OTHER INFORMATION: Description of Artificial Sequence:C-type retrovirus murine leukemia virus (MLV) fusogenic membrane envelope glycoprotein (FMG) domain

<400> SEQUENCE: 6
acttgtggtc tcgctgttcc ttgggagggt ctcctctgag tgattgacta ccgtcagcgg 60
gggtctttca tttgggggct cgtccgggat cgggagaccc ctgcccaggg accaccgacc 120
caccaccggg agctcactta caggcccttc aagcagtaca acgagaggtc tggaagccac 180
tggctgcggc ctatcaggac cagcaagacc agccagtgat accacacccc ttccgtgtcg 240
gcgacaccgt gtgggtacgc cggcaccaga ctaagaactt ggaacctcgt tggaaaggac 300

-continued

```
cctataccgt cctgctgacc acccccaccg ctctcaaagt agacggcatc gctgcgtgga    360
tccacgccgc tcacgtaaag gcggcgacaa cccctccggc cggaacagca tcaggaccga    420
catggaaggt ccagcgttct caaaacccct taaagataag attaacccgt ggggccccct    480
gatagtcctg ggatcttaa taagggcagg agtatcagta caacatgaca gccctcacca    540
ggtcttcaat gttacttgga gagttaccaa cttaatgaca ggacaaacag ctaacgctac    600
ctccctcctg ggacaatga cagatgcctt tcctatgctg tacttcgact tgtgcgattt    660
aatagggac gattgggatg agactggact tgggtgtcgc actcccgggg gaagaaaacg    720
ggcaagaaca tttgacttct atgtttgccc cgggcatact gtaccaacag ggtgtggagg    780
gccgagagag ggctactgtg gcaaatgggg ctgtgagacc actggacagg catactggaa    840
gccatcatca tcatgggacc taatttccct taagcgagga aacacccctc ggaatcaggg    900
cccctgttat gattcctcag tggtctccag tggcatccag ggtgccacac cggggggtcg    960
atgcaatccc ctagtcctag aattcactga cgcgggtaaa aaggccagct gggatggccc   1020
caaagtatgg ggactaagac tgtaccaatc cacagggatc gacccggtga cccggttctc   1080
tttgacccgc caggtcctca atatagggcc ccgcatcccc attgggccta atcccgtgat   1140
cactggccaa ctacccccct cccgacccgt gcagatcagg ctccccaggc ctcctcagac   1200
tcctcctaca ggcgcagcct ctatggtccc tgggactgcc ccaccgtctc aacaacctgg   1260
gacgggagac aggctgctaa acctggtaga tggagcatac caagcactca acctcaccag   1320
tcctgacaaa acccaagagt gctggttgtg tctggtatcg ggacccccct actacgaagg   1380
ggttgccgtc ctaggtactt actccaacca tacctctgcc ccagctaact gctccgcggc   1440
ctcccaacac aagctgaccc tgtccgaagt aaccggacag ggactctgcg taggagcagt   1500
tcccaaaacc catcaggccc tgtgtaatac cacccaaaag acgagcgacg ggtcctacta   1560
tctggctgct cccgccggga ccatttgggc ttgcaacacc gggctcactc cctgcctatc   1620
tactactgta ctcaatctaa ccacagatta ttgtgtatta gttgaactct ggcccagagt   1680
aatttaccac tcccccgatt atatgtatgg tcagcttgaa cagcgtacca aatataaaag   1740
agagccagta tcattgaccc tggcccttct actaggagga ttaaccatgg gagggattgc   1800
agctggaata gggacgggga ccactgcctt aattaaaacc cagcagtttg agcagcttca   1860
tgccgctatc cagacagacc tcaacgaagt cgaaaagtca attaccaacc tagaaaagtc   1920
actgacctcg ttgtctgaag tagtcctaca gaaccgcaga ggcctagatt tgctattcct   1980
aaaggaggga ggtctctgcg cagccctaaa agaagaatgt tgtttttatg cagaccacac   2040
ggggctagtg agagacagca tggccaaatt aagagaaagg cttaatcaga gacaaaaact   2100
atttgagaca ggccaaggat ggttcgaagg gctgtttaat agatccccct ggtttaccac   2160
cttaatctcc accatcatgg gacctctaat agtactctta ctgatcttac tctttggacc   2220
ttgcattctc aatcgattag tccaatttgt taaagacagg atatcagtgg tccaggctct   2280
agttttgact caacaatatc accagctgaa gcctatagag tacgagccat agataaaata   2340
aaagatttta tttagtctcc agaaaaaggg gggaatgaaa gaccccacct gtaggtttgg   2400
caagctagct taacgccatt ttgcaaggca tggaaaaata cataactgag aatagagaag   2460
ttcagatcaa ggtcaggaac agatggaaca gctgaatatg ggccaaacag gatatctgtg   2520
gtaagcagtt cctgccccgg ctcagggcca agaacagatg gaacagctga atatgggcca   2580
aacaggatat ctgtggtaag cagttcctgc cccggctcag ggccaagaac agatggtccc   2640
cagatgcggt ccagccctca gcagtttcta gagaaccatc agatgtttcc agggtgcccc   2700
```

```
aaggacctga aatgaccctg tgccttattt gaactaacca atcagttcgc ttctcgcttc   2760

tgttcgcgcg cttctgctcc ccgagctcaa taaaagagcc cacaacccct cactcggggc   2820

gccagtcctc cgattgactg agtcgcccgg gtacccgtgt atccaataaa ccctcttgca   2880

gttgcatccg                                                          2890
```

<210> SEQ ID NO 7
<211> LENGTH: 2384
<212> TYPE: DNA
<213> ORGANISM: Measles virus
<220> FEATURE:
<221> NAME/KEY: misc_feature
<223> OTHER INFORMATION: Measles virus fusion protein

<400> SEQUENCE: 7

```
tcgagggcca aggaacatac acacccaaca gaacccagac cccggcccac ggcgccgcgc     60

ccccaacccc cgacaaccag agggagcccc caaccaatcc gccggctccc ccggtgccca    120

caggcaggga caccaacccc cgaacagacc cagcacccaa ccatcgacaa tccaagacgg    180

gggggccccc ccaaaaaaaa ggcccccagg ggccgacagc cagcaccgcg aggaagccca    240

cccaccccac acacgaccac ggcaaccaaa ccagaaccca gaccaccctg ggtcaccagc    300

tccagacctc ggtcatcacc ccgcagaaag gaaaggcaca acccgcgacc ccagccccga    360

tccggcgggg agccacccaa cccgaaccag cacccaagag cgatccccga aggacccccg    420

aaccgcaaag gacatcagta tcccacagcc tctccaagtc ccccggtctc ctcctcttct    480

cgaagggacc aaaagatcaa tccaccacca cacacccgac gacactcaac tccccacccc    540

taaaggagac accgggaatc ccagaatcaa gactcatcca atgtccatca tgggtctcaa    600

ggtgaacgtc tctgccatat tcatggcagt actgttaact ctccaaacac ccaccggtca    660

aatccattgg ggcaatctct ctaagatagg ggtggtagga ataggaagtg caagctacaa    720

agttatgact cgttccagcc atcaatcatt agtcataaaa ttaatgccca atataactct    780

cctcaataac tgcacgaggg tagagattgc agaatacagg agactactga gaacagtttt    840

ggaaccaatt agagatgcac ttaatgcaat gacccagaat ataagaccgg ttcagagtgt    900

agcttcaagt aggagacaca agagatttgc gggagtagtc ctggcaggtg cggccctagg    960

cgttgccaca gctgctcaga taacagccgg cattgcactt caccagtcca tgctgaactc   1020

tcaagccatc gacaatctga gagcgagcct ggaaactact aatcaggcaa ttgaggcaat   1080

cagacaagca gggcaggaga tgatattggc tgttcagggt gtccaagact acatcaataa   1140

tgagctgata ccgtctatga accaactatc ttgtgattta atcggccaga agctcgggct   1200

caaattgctc agatactata cagaaatcct gtcattattt ggccccagct tacgggaccc   1260

catatctgcg gagatatcta tccaggcttt gagctatgcg cttggaggag acatcaataa   1320

ggtgttagaa aagctcggat acagtggagg tgatttactg ggcatcttag agagcagagg   1380

aataaaggcc cggataactc acgtcgacac agagtcctac ttcattgtcc tcagtatagc   1440

ctatccgacg ctgtccgaga ttaagggggt gattgtccac cggctagagg gggtctcgta   1500

caacataggc tctcaagagt ggtataccac tgtgcccaag tatgttgcaa cccaagggta   1560

ccttatctcg aattttgatg agtcatcgtg tactttcatg ccagagggga ctgtgtgcag   1620

ccaaaatgcc ttgtacccga tgagtcctct gctccaagaa tgcctccggg ggtccaccaa   1680

gtcctgtgct cgtacactcg tatccgggtc ttttgggaac cggttcattt tatcacaagg   1740

gaacctaata gccaattgtg catcaatcct ttgcaagtgt tacacaacag gaacgatcat   1800
```

taatcaagac cctgacaaga tcctaacata cattgctgcc gatcactgcc cggtagtcga 1860
ggtgaacggc gtgaccatcc aagtcgggag caggaggtat ccagacgctg tgtacttgca 1920
cagaattgac ctcggtcctc ccatatcatt ggagaggttg gacgtaggga caaatctggg 1980
gaatgcaatt gctaagttgg aggatgccaa ggaattgttg gagtcatcgg accagatatt 2040
gaggagtatg aaaggtttat cgagcactag catagtctac atcctgattg cagtgtgtct 2100
tggagggttg atagggatcc ccgctttaat atgttgctgc agggggcgtt gtaacaaaaa 2160
gggagaacaa gttggtatgt caagaccagg cctaaagcct gatcttacgg gaacatcaaa 2220
atcctatgta aggtcgctct gatcctctac aactcttgaa acacaaatgt tcccacaagt 2280
ctcctcttcg tcatcaagca accaccgcac ccagcatcaa gcccacctga accagctaaa 2340
ttatctccgg cttccctctg gccgaacaat atcggtagtt aatt 2384

<210> SEQ ID NO 8
<211> LENGTH: 2535
<212> TYPE: DNA
<213> ORGANISM: Human immunodeficiency virus
<220> FEATURE:
<221> NAME/KEY: misc_feature
<223> OTHER INFORMATION: HIV gp160

<400> SEQUENCE: 8
atgagagtga tggggataca gaggaattgg ccacaatggt ggatatgggg caccttaggc 60
ttttggatga taataatttg tagggtggtg ggaacttga acttgtgggt cacagtctat 120
tatggggtac ctgtgtggaa agaagcaaaa actactctat tctgtgcatc agatgctaaa 180
gcatatgata aagaagtaca taatgtctgg gctacacatg cctgtgtacc cacagacccc 240
aacccacgag aaatagtttt ggaaaatgta acagaaaatt ttaacatgtg gaaaaatgac 300
atggtggatc agatgcatga ggatataatc agtttatggg atcaaagcct aaaaccatgt 360
gtaaagttga ccccactctg tgtcacttta aattgtacaa atgcacctgc ctacaataat 420
agcatgcatg gagaaatgaa aaattgctct ttcaatacaa ccacagagat aagagatagg 480
aaacagaaag cgtatgcact tttttataaa cctgatgtag tgccacttaa taggagagaa 540
gagaataatg ggacaggaga gtatatatta ataaattgca attcctcaac cataacacaa 600
gcctgtccaa aggtcacttt tgacccaatt cctatacatt attgtgctcc agctggttat 660
gcgattctaa agtgtaataa taagacattc aatgggacag gaccatgcaa taatgtcagc 720
acagtacaat gtacacatgg aattatgcca gtggtatcaa ctcaattact gttaaatggt 780
agcctagcag aagaagagat aataattaga tctgaaaatc tgacaaacaa tatcaaaaca 840
ataatagtcc accttaataa atctgtagaa attgtgtgta caagacccaa caataataca 900
agaaaaagta taaggatagg accaggacaa acattctatg caacaggtga aataatagga 960
aacataagag aagcacattg taacattagt aaaagtaact ggaccagtac tttagaacag 1020
gtaaagaaaa aattaaaaga acactacaat aagacaatag aatttaaccc accctcagga 1080
ggggatctag aagttacaac acatagcttt aattgtagag gagaattttt ctattgcaat 1140
acaacaaaac tgttttcaaa caacagtgat tcaaacaacg aaaccatcac actcccatgc 1200
aagataaaac aaattataaa catgtggcag aaggtaggac gagcaatgta tgcccctccc 1260
attgaaggaa acataacatg taaatcaaat atcacaggac tactattgac acgtgatgga 1320
ggaaagaata caacaaatga gatattcaga ccgggaggag gaaatatgaa ggacaattgg 1380
agaagtgaat tatataaata taaagtggta gaaattgagc cattgggagt agcacccact 1440

```
aaatcaaaaa ggagagtggt ggagagagaa aaaagagcag tgggactagg agctgtactc   1500

cttgggttct tgggagcagc aggaagcact atgggcgcgg cgtcaataac gctgacggta   1560

caggccagac aactgttgtc tggtatagtg caacagcaaa gcaatttgct gagagctata   1620

gaggcgcaac agcatatgtt gcaactcacg gtctggggca ttaagcagct ccagacaaga   1680

gtcttggcta tagagagata cctaaaggat caacagctcc tagggctttg ggctgctct    1740

ggaaaaatca tctgcaccac tgctgtgcct tggaactcca gttggagtaa taaatctcaa   1800

gaagatattt gggataacat gacctggatg cagtgggata gagaaattag taattacaca   1860

ggcacaatat ataggttact tgaagactcg caaaaccagc aggagaaaaa tgaaaaagat   1920

ttattagcat tggacagttg gaaaaacttg tggaattggt ttaacataac aaattggctg   1980

tggtatataa aaatattcat catgatagta ggaggcttga taggtttgag aataattttt   2040

ggtgtactcg ctatagtgaa aagagttagg cagggatact cacctttgtc gtttcagacc   2100

cttaccccaa gcccgagggg tcccgacagg ctcggaagaa tcgaagaaga aggtggagag   2160

caagacaaag acagatccat tcgattagtg agcggattct tagcacttgc ctgggacgat   2220

ctgcggagcc tgtgcctctt cagctaccac cacttgagag acttcatatt gattgcagcg   2280

agagcagcgg aacttctggg acgcagcagt ctcaggggac tgcagagagg gtgggaagcc   2340

cttaagtatc tgggaaatct tgtgcagtat gggggtctgg agctaaaaag aagtgctatt   2400

aaactgtttg ataccatagc aatagcagta gctgaaggaa cagataggat tcttgaagta   2460

atacagagaa tttgtagagc tatccgccac atacctataa gaataagaca gggctttgaa   2520

gcagctttgc aataa                                                    2535


<210> SEQ ID NO 9
<211> LENGTH: 2577
<212> TYPE: DNA
<213> ORGANISM: Simian immunodeficiency virus
<220> FEATURE:
<221> NAME/KEY: misc_feature
<223> OTHER INFORMATION: SIV gp160
<220> FEATURE:
<221> NAME/KEY: modified_base
<222> LOCATION: (1)..(2577)
<223> OTHER INFORMATION: n = g, a, c or t
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (1445)..(1445)
<223> OTHER INFORMATION: n is a, c, g, or t
<220> FEATURE:
<221> NAME/KEY: misc_feature
<222> LOCATION: (1473)..(1473)
<223> OTHER INFORMATION: n is a, c, g, or t
<220> FEATURE:
<221> NAME/KEY: misc_feature
<222> LOCATION: (1612)..(1612)
<223> OTHER INFORMATION: n is a, c, g, or t
<220> FEATURE:
<221> NAME/KEY: misc_feature
<222> LOCATION: (2532)..(2532)
<223> OTHER INFORMATION: n is a, c, g, or t

<400> SEQUENCE: 9

atgaggaagc cgatacatat tatttggggt ctggctttgc taatccagtt tatagagaag     60

gggacgaatg aagactatgt aacagtattc tatggagtcc ctgtctggag aaatgcgaca    120

cctactctat tttgtgccac aaatgcctcc atgacaagta cagaggtgca caatgtatgg    180
```

```
gcaactacca gttgtgtgcc aatagatcca gatcctattg tagttaggct caatacctca    240
gtctggttta atgcttataa aaattatatg gtagaaagta tgacagaaga tatgntacaa    300
ttattccaac aaagccataa gccatgtgta aaactaacac ctatgtgtat aaaaatgaat    360
tgtacaggat acaatggaac acctacaaca ccaagtacaa caacaagtac agtaacacca    420
aagacaacaa caccaatagt agatggcatg aagctacaag aatgtaactt taatcagagc    480
acaggattta aagataagaa acaaaaaatg aaagccatat tttataaagg agatcttatg    540
aagtgtcagg acaacaatga gactaactgc tattacttat ggcactgcaa caccacaact    600
atcacacaat cctgtgaaaa gtctactttt gaaccaattc ctatacatta ttgtgctcca    660
gcaggatatg ctatattgag atgtgaagat gaggatttta caggagtagg gatgtgtaaa    720
aatgtctcag tagtacattg cactcatgga ataagcccaa tggtggcaac atggttacta    780
ttaaatggaa cttaccaaac aaacacttca gtagtaatga atggtcgcaa aaatgaatct    840
gtgcttgtaa gatttggaaa agaattcgaa aacttaacaa ttacatgtat aagaccagga    900
aataggacag taagaaatct acaaatagga ccaggaatga ctttctataa cgtagaaata    960
gcaacaggag acactaggaa agcgttctgt acagtcaata agacgctatg ggaacaagca   1020
cgtaacaaaa cagagcacgt tcttgcggag cattggaaaa aagtagacaa caaaaccaat   1080
gcgaaaacaa tatggacatt ccaagatgga gatcctgaag taaaagtgca ttggtttaat   1140
tgccaaggag aattctttta ttgtgatata acaccttggt tcaatgccac atacacggga   1200
aacctcatca caaacggagc cctcatagca cattgcagaa ttaagcagat agttaatcat   1260
tggggcatag tttcaaaagg catttactta gcccctagga gagggaatgt ttcctgtact   1320
tccagcataa ctggaattat gttggaaggt caaatatata atgaaactgt taaagtgtca   1380
cctgctgcaa gagtagcaga ccaatggaga gcggagttgt ccaggtacca ggtggtagag   1440
attgntccct tgtcagtagc cccaacaaca ggnaaaaggc cagaaataaa acaacactcc   1500
agacaaaaaa gaggcattgg aatagggctg ttcttcttgg gtcttctcag tgcagctggc   1560
agtacaatgg gcgcagcgtc aatagcgctg acggcacaga ccaggaattt gntccatggt   1620
attgtacaac agcaggccaa tctgctgcaa gccatagaga cacagcaaca tctgctacag   1680
ctctcggtct ggggagtaaa acaactccag gcaagaatgc ttgcagtcga gaagtaccta   1740
agagatcaac aactattgag cctctggggt tgtgctgaca aggtgacctg tcacactacg   1800
gtgccttgga ataattcctg ggtaaacttc acgcaaacat gtgcaaagaa cagcagtgat   1860
atacaatgta tttgggaaaa tatgacatgg caagaatggg acagattagt acagaattca   1920
acaggacaga tatataatat cttacaaata gcacatgagc aacaagagag aaataaaaag   1980
gaattatatg aactagacaa atggagctca ttatggaatt ggtttgacat aacacaatgg   2040
ctatggtata taaaaatatt tattatgata gtaggagcta ttgtaggact aagaattttg   2100
cttgtattag ttagttgctt aagaaaggtt aggcagggat atcatcctct gtcatttcag   2160
atccctaccc aaaaccagca ggatccagag cagccagaag aaataagaga agaaggtgga   2220
agaaaagaca ggatcaggtg gagggccttg cagcacgggt tcttcgcact cttgtgggtg   2280
gacctgacga gcataatcca gtggatctac cagatctgca gaacctgtct cttgaacctt   2340
tgggcagtcc tccaacacct ctgcagaatt actttcagac tgtgcaacca tctggagaac   2400
aatctcagca ccctctggac aataatcaga actgagatca ttaagaacat tgacagactt   2460
gctattttgg taggggaaaa aacagatagc attcctctag ctctccaaac tattgtcaga   2520
```

atcataaggg angtccctag gcgcatcaga cargggttgg aaattgcatt waattaa 2577

<210> SEQ ID NO 10
<211> LENGTH: 262
<212> TYPE: DNA
<213> ORGANISM: Human immunodeficiency virus
<220> FEATURE:
<221> NAME/KEY: misc_feature
<223> OTHER INFORMATION: HIV retroviral env protein

<400> SEQUENCE: 10
ggatcaaagt ctaaagccat gtgtaaaatt aaccccactc tgtgttactt taagttgcga 60
taatgtgaat attactactg ccaatactac caataccact agtaggcatg ggaaactgat 120
ggagccagga gaaataaaaa actgctcttt caatatcacc acagacttga gagataagat 180
gaagaaagaa tatgcacttt tttataacct tgatgtagta caaataaatg atgataatac 240
tacctatagg ttgataagtt gt 262

<210> SEQ ID NO 11
<211> LENGTH: 2360
<212> TYPE: DNA
<213> ORGANISM: Ebola virus
<220> FEATURE:
<221> NAME/KEY: misc_feature
<223> OTHER INFORMATION: Reston Ebola virus glycoprotein (Gp)

<400> SEQUENCE: 11
atacgatgaa gattaaggcg acaacgagcc gaaacttcat ctcttttaaa gatctaacat 60
tatctgttcc aaagtcatac aaggacacat tcaaatcagg gattgtaagc tgctatttct 120
tacctcccca aattacctat acaacatggg gtcaggatat caacttctcc aattgcctcg 180
ggaacgtttt cgtaaaactt cgttcttagt atgggtaatc atcctcttcc agcgagcaat 240
ctccatgccg cttggtatag tgacaaatag cactctcaaa gcaacagaaa ttgatcaatt 300
ggtttgtcgg gacaaactgt catcaaccag tcagctcaag tctgtggggc tgaatctgga 360
aggaaatgga attgcaaccg atgtcccatc agcaacaaaa cgctggggat ttcgttcagg 420
tgtgcctccc aaggtggtca gctatgaagc cggagaatgg gcagaaaatt gctacaatct 480
ggagatcaaa aagtcagacg gaagtgaatg cctccctctc cctcccgacg gtgtacgagg 540
attccctaga tgtcgctatg tccacaaagt tcaaggaaca ggtccttgtc ccggtgactt 600
agctttccat aaaaatgggg ctttttttctt gtatgataga ttggcctcaa ctgtcatcta 660
ccgagggaca actttttgctg aaggtgtcgt agctttttta attctgtcag agcccaagaa 720
gcatttttgg aaggctacac cagctcatga accggtgaac acaacagatg attccacaag 780
ctactacatg accctgacac tcagctacga gatgtcaaat tttgggggca atgaaagtaa 840
cacccttttt aaggtagaca accacacata tgtgcaacta gatcgtccac acactccgca 900
gttccttgtt cagctcaatg aaacacttcg aagaaataat cgccttagca acagtacagg 960
gagattgact tggacattgg atcctaaaat tgaaccagat gttggtgagt gggccttctg 1020
ggaaactaaa aaaacttttc ccaacaactt catggagaaa acttgcattt ccaaattcta 1080
tcaacccaca ccaacaactc ctcagatcag agcccggcgg gaactgtcca aggaaaaatt 1140
agctaccacc cacccgccaa caactccgag ctggttccaa cggattcccc tccagtggtt 1200
tcagtgctca ctgcaggacg gacagaggaa atgtcgaccc aaggtctaac caacggagag 1260
acaatcacag gtttcaccgc gaacccaatg acaaccacca ttgccccaag tccaaccatg 1320
acaagcgagg ttgataacaa tgtaccaagt gaacaaccga acaacacagc atccattgaa 1380

-continued gactcccccc catcggcaag caacgagaca atttaccact ccgagatgga tccgatccaa 1440
ggctcgaaca actccgccca gagcccacag accaagacca cgccagcacc cacaacatcc 1500
ccgatgaccc aggacccgca agagacggcc aacagcagca aaccaggaac cagcccagga 1560
agcgcagccg gaccaagtca gcccggactc actataaata cagtaagtaa ggtagctgat 1620
tcactgagtc ccaccaggaa acaaaagcga tcggttcgac aaaacaccgc taataaatgt 1680
aacccagatc tttactattg gacagctgtt gatgaggggg cagcagtagg attggcatgg 1740
attccatatt tcggacctgc agcagaaggc atctacattg agggtgtaat gcataatcag 1800
aatgggctta tttgcgggct acgtcagcta gccaatgaaa ctacccaggc tcttcaatta 1860
tttctgcggg ccacaacaga actgaggact tactcacttc ttaacagaaa agctattgat 1920
tttcttcttc aacgatgggg aggtacctgt cgaatcctag gaccatcttg ttgcattgag 1980
ccacatgatt ggacaaaaaa tattactgat gaaattaacc aaattaaaca tgactttatt 2040
gacaatcccc taccagacca cggagatgat cttaatctat ggacaggttg gagacaatgg 2100
atcccggctg gaattgggat tattggagtt ataattgcta taatagccct actttgtata 2160
tgtaagattt tgtgttgatt tattctgaga tctgagagag aaaaatctca gggttactct 2220
aaggagaaat attattttta aaatttactt gaatgctgac cacttatctt aaatgagcaa 2280
ttaataatat gtttttctgc ttctttgctt gatttacaat atgatatttc tcttaataat 2340
gattaatata ttaagaaaaa 2360

<210> SEQ ID NO 12
<211> LENGTH: 1733
<212> TYPE: DNA
<213> ORGANISM: Influenza A virus
<220> FEATURE:
<221> NAME/KEY: misc_feature
<223> OTHER INFORMATION: Influenza A virus (A/duck/Alberta/35/76(H1N1)) haemagglutinin (HA1 and HA2 chains)

<400> SEQUENCE: 12
agcaaaagca ggggataatc aaatcaatcg agatggaagc aaaactattt gtactattct 60
gtacattcac tgtactgaaa gctgacacca tctgtgtggg ctaccatgca aacaactcta 120
cagacactgt tgacacagta ctggaaaaga atgtgaccgt gactcactca gtgaatttgc 180
tcgaagacag ccataatggg aaactctgca gcctgaacgg gatagctccc ctacaactgg 240
gaaagtgcaa tgtggcggga tggctcctgg gcaatccaga gtgtgatctt ctactcactg 300
caaactcatg gtcctacata atagaaactt caaactcaga aaacggaaca tgctaccccg 360
gtgaattcat agattatgaa gaattaagag agcagctaag ttcaatttct tcatttgaaa 420
aatttgaaat tttcccgaag gcaagctcat ggccaaatca tgagacaact aaaggtgtta 480
cagctgcatg ctcttactct ggagccagca gtttttaccg gaatttgctg tggataacaa 540
agaaagggac ttcatatcca aaactcagca aatcatacac gaacaataag gggaaagaag 600
tgcttgtgct ctgggggtg caccaccctc caagtgtcag tgagcaacaa agtctatacc 660
agaatgctga tgcatacgtt tcagttggat cgtcaaaata caaccgaaga ttcgctccgg 720
aaatagcagc tagacctgaa gttagaggac aggcaggcag aatgaactat tattggacac 780
tattagacca aggagacact ataacatttg aagccactgg gaatttgata gcaccatggt 840
atgctttcgc attgaataag gggtctgact ctggaattat aacatcagat gctccagttc 900
acaattgtga cacaaggtgc caaacccctc atggggcttt gaacagcagc cttccttttc 960

-continued

```
agaatgtaca tcctatcact attggagaat gtcccaaata cgtcaagagc accaaactaa   1020
gaatggcaac aggactaaga aatgtcccat ccattcagtc cagaggacta tttggagcaa   1080
ttgctggatt cattgaggga ggatggacag gcatgataga tggatggtac gggtatcatc   1140
atcagaatga gcaaggatca ggatatgctg ctgatcagaa aagcacacag aatgcgatcg   1200
acgggatcac aagtaaggtg aattcggtaa ttgaaaagat gaacactcaa ttcactgcag   1260
tgggcaaaga attcaataat ttagaaagga gaattgaaaa tttgaataaa aaggtcgatg   1320
atggattcct ggatgtttgg acatacaatg ccgaactgct cgtcctactt gaaaatgaaa   1380
gaactctaga ctttcatgac tccaatgtga gaaatttata tgagaaggtc aaatcgcaat   1440
tgaggaataa tgccaaagaa attgggaatg gttgttttga gttctaccac aagtgtgatg   1500
atgagtgcat ggaaagtgtg aagaacggca catacgacta ccccaagtat tcagaagagt   1560
ccaaattgaa tcgagaagaa atagacgggg tgaaactaga atcaatggga gtttatcaaa   1620
ttttggcgat ctattccaca gtcgccagtt ctctagtctt gttagtctcc tggggggcaa   1680
tcagcttctg gatgtgctct aatgggtcat tgcaatgcag aatatgcatt taa          1733

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:synthetic
      amplification primer for ribonucleotide reductase (RR) domain and
      right-flanking region of Herpes simplex virus-2 (HSV-2)
      ribonucleotide reductase large subunit (ICP10, RR1)

<400> SEQUENCE: 13
acacgcccta tcatctgagg                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:synthetic
      amplification primer for ribonucleotide reductase (RR) domain and
      right-flanking region of Herpes simplex virus-2 (HSV-2)
      ribonucleotide reductase large subunit (ICP10, RR1)

<400> SEQUENCE: 14
aacatgatga aggggcttcc                                                  20

<210> SEQ ID NO 15
<211> LENGTH: 502
<212> TYPE: PRT
<213> ORGANISM: human herpesvirus 2
<220> FEATURE:
<221> NAME/KEY: misc_feature
<223> OTHER INFORMATION: Herpes simplex virus type 2 (HSV-2)
      ribonucleotide reductase (ICP10, RR1)
<220> FEATURE:
<221> NAME/KEY: MOD_RES
<222> LOCATION: (280)..(280)
<223> OTHER INFORMATION: Xaa = any amino acid
<400> SEQUENCE: 15

Met Ala Asn Arg Pro Ala Ala Ser Ala Leu Ala Gly Ala Arg Ser Pro
1               5                   10                  15

Ser Glu Arg Gln Glu Pro Arg Glu Pro Glu Val Ala Pro Pro Gly Gly
            20                  25                  30

Asp His Val Phe Cys Arg Lys Val Ser Gly Val Met Val Leu Ser Ser
```

```
        35                  40                  45

Asp Pro Pro Gly Pro Ala Ala Tyr Arg Ile Ser Asp Ser Ser Phe Val
    50                  55                  60

Gln Cys Gly Ser Asn Cys Ser Met Ile Ile Asp Gly Asp Val Ala Arg
65                  70                  75                  80

Gly His Leu Arg Asp Leu Glu Gly Ala Thr Ser Thr Gly Ala Phe Val
                85                  90                  95

Ala Ile Ser Asn Val Ala Ala Gly Gly Asp Gly Arg Thr Ala Val Val
            100                 105                 110

Ala Leu Gly Gly Thr Ser Gly Pro Ser Ala Thr Thr Ser Val Gly Thr
        115                 120                 125

Gln Thr Ser Gly Glu Phe Leu His Gly Asn Pro Arg Thr Pro Glu Pro
    130                 135                 140

Gln Gly Pro Gln Ala Val Pro Pro Pro Pro Pro Pro Pro Phe Pro Trp
145                 150                 155                 160

Gly His Glu Cys Cys Ala Arg Arg Asp Ala Arg Gly Gly Ala Glu Lys
                165                 170                 175

Asp Val Gly Ala Ala Glu Ser Trp Ser Asp Gly Pro Ser Ser Asp Ser
            180                 185                 190

Glu Thr Glu Asp Ser Asp Ser Ser Asp Glu Asp Thr Gly Ser Gly Ser
        195                 200                 205

Glu Thr Leu Ser Arg Ser Ser Ser Ile Trp Ala Ala Gly Ala Thr Asp
    210                 215                 220

Asp Asp Asp Ser Asp Ser Asp Ser Arg Ser Asp Asp Ser Val Gln Pro
225                 230                 235                 240

Asp Val Val Val Arg Arg Arg Trp Ser Asp Gly Pro Ala Pro Val Ala
                245                 250                 255

Phe Pro Lys Pro Arg Arg Pro Gly Asp Ser Pro Gly Asn Pro Gly Leu
            260                 265                 270

Gly Ala Ala Pro Gly Arg Ala Xaa Pro Arg Arg Thr Arg Ala Arg Arg
        275                 280                 285

Pro Thr Pro Ile Pro Ala His Ala Ala Ala Pro Gln Ala Asp Val Ala
    290                 295                 300

Pro Val Leu Asp Gly Gln Pro Thr Val Gly Thr Asp Pro Gly Tyr Pro
305                 310                 315                 320

Val Pro Leu Glu Leu Thr Pro Glu Asn Ala Glu Ala Val Ala Arg Phe
                325                 330                 335

Leu Gly Asp Ala Val Asp Arg Glu Pro Ala Leu Met Leu Glu Tyr Phe
            340                 345                 350

Cys Arg Cys Ala Arg Glu Glu Ser Lys Arg Val Pro Pro Arg Thr Phe
        355                 360                 365

Gly Ser Ala Pro Arg Leu Thr Glu Asp Asp Phe Gly Leu Leu Asn Tyr
    370                 375                 380

Ala Leu Ala Glu Met Arg Arg Leu Cys Leu Asp Leu Pro Pro Val Pro
385                 390                 395                 400

Pro Asn Ala Tyr Thr Pro Tyr His Leu Arg Glu Tyr Ala Thr Arg Leu
                405                 410                 415

Val Asn Gly Phe Lys Pro Leu Val Arg Arg Ser Ala Arg Leu Tyr Arg
            420                 425                 430

Ile Leu Gly Ile Leu Val His Leu Arg Ile Arg Thr Arg Glu Ala Ser
        435                 440                 445

Phe Glu Glu Trp Met Arg Ser Lys Glu Val Asp Leu Asp Phe Gly Leu
    450                 455                 460
```

Thr Glu Arg Leu Arg Glu His Glu Ala Gln Leu Met Ile Leu Ala Gln
465 470 475 480

Ala Leu Asn Pro Tyr Asp Cys Leu Ile His Ser Thr Pro Asn Thr Leu
485 490 495

Val Glu Arg Gly Leu Gln
500

<210> SEQ ID NO 16
<211> LENGTH: 4151
<212> TYPE: DNA
<213> ORGANISM: Artificial Sequence
<220> FEATURE:
<223> OTHER INFORMATION: Description of Artificial Sequence:enhanced green fluorescent protein (EGPF) cloning vector pEGFP-1 coding sequence

<400> SEQUENCE: 16
tagttattac tagcgctacc ggactcagat ctcgagctca agcttcgaat tctgcagtcg 60
acggtaccgc gggcccggga tccaccggtc gccaccatgg tgagcaaggg cgaggagctg 120
ttcaccgggg tggtgcccat cctggtcgag ctggacggcg acgtaaacgg ccacaagttc 180
agcgtgtccg gcgagggcga gggcgatgcc acctacggca agctgaccct gaagttcatc 240
tgcaccaccg gcaagctgcc cgtgccctgg cccaccctcg tgaccaccct gacctacggc 300
gtgcagtgct tcagccgcta ccccgaccac atgaagcagc acgacttctt caagtccgcc 360
atgcccgaag gctacgtcca ggagcgcacc atcttcttca aggacgacgg caactacaag 420
acccgcgccg aggtgaagtt cgagggcgac accctggtga accgcatcga gctgaagggc 480
atcgacttca aggaggacgg caacatcctg gggcacaagc tggagtacaa ctacaacagc 540
cacaacgtct atatcatggc cgacaagcag aagaacggca tcaaggtgaa cttcaagatc 600
cgccacaaca tcgaggacgg cagcgtgcag ctcgccgacc actaccagca gaacaccccc 660
atcggcgacg gccccgtgct gctgcccgac aaccactacc tgagcaccca gtccgccctg 720
agcaaagacc ccaacgagaa gcgcgatcac atggtcctgc tggagttcgt gaccgccgcc 780
gggatcactc tcggcatgga cgagctgtac aagtaaagcg gccgcgactc tagatcataa 840
tcagccatac cacatttgta gaggttttac ttgctttaaa aaacctccca cacctccccc 900
tgaacctgaa acataaaatg aatgcaattg ttgttgttaa cttgtttatt gcagcttata 960
atggttacaa ataaagcaat agcatcacaa atttcacaaa taaagcattt ttttcactgc 1020
attctagttg tggtttgtcc aaactcatca atgtatctta aggcgtaaat tgtaagcgtt 1080
aatattttgt taaaattcgc gttaaatttt tgttaaatca gctcattttt taaccaatag 1140
gccgaaatcg gcaaaatccc ttataaatca aaagaataga ccgagatagg gttgagtgtt 1200
gttccagttt ggaacaagag tccactatta aagaacgtgg actccaacgt caaagggcga 1260
aaaaccgtct atcagggcga tggcccacta cgtgaaccat caccctaatc aagttttttg 1320
gggtcgaggt gccgtaaagc actaaatcgg aaccctaaag ggagcccccg atttagagct 1380
tgacggggaa agccggcgaa cgtggcgaga aaggaaggga agaaagcgaa aggagcgggc 1440
gctagggcgc tggcaagtgt agcggtcacg ctgcgcgtaa ccaccacacc cgccgcgctt 1500
aatgcgccgc tacagggcgc gtcaggtggc acttttcggg gaaatgtgcg cggaacccct 1560
atttgtttat ttttctaaat acattcaaat atgtatccgc tcatgagaca ataaccctga 1620
taaatgcttc aataatattg aaaaaggaag agtcctgagg cggaaagaac cagctgtgga 1680
atgtgtgtca gttagggtgt ggaaagtccc caggctcccc agcaggcaga agtatgcaaa 1740

-continued

```
gcatgcatct caattagtca gcaaccaggt gtggaaagtc cccaggctcc ccagcaggca   1800
gaagtatgca aagcatgcat ctcaattagt cagcaaccat agtcccgccc ctaactccgc   1860
ccatcccgcc cctaactccg cccagttccg cccattctcc gccccatggc tgactaattt   1920
tttttattta tgcagaggcc gaggccgcct cggcctctga gctattccag aagtagtgag   1980
gaggcttttt tggaggccta ggcttttgca aagatcgatc aagagacagg atgaggatcg   2040
tttcgcatga ttgaacaaga tggattgcac gcaggttctc cggccgcttg ggtggagagg   2100
ctattcggct atgactgggc acaacagaca atcggctgct ctgatgccgc cgtgttccgg   2160
ctgtcagcgc aggggcgccc ggttcttttt gtcaagaccg acctgtccgg tgccctgaat   2220
gaactgcaag acgaggcagc gcggctatcg tggctggcca cgacgggcgt tccttgcgca   2280
gctgtgctcg acgttgtcac tgaagcggga agggactggc tgctattggg cgaagtgccg   2340
gggcaggatc tcctgtcatc tcaccttgct cctgccgaga aagtatccat catggctgat   2400
gcaatgcggc ggctgcatac gcttgatccg gctacctgcc cattcgacca ccaagcgaaa   2460
catcgcatcg agcgagcacg tactcggatg gaagccggtc ttgtcgatca ggatgatctg   2520
gacgaagagc atcaggggct cgcgccagcc gaactgttcg ccaggctcaa ggcgagcatg   2580
cccgacggcg aggatctcgt cgtgacccat ggcgatgcct gcttgccgaa tatcatggtg   2640
gaaaatggcc gcttttctgg attcatcgac tgtggccggc tgggtgtggc ggaccgctat   2700
caggacatag cgttggctac ccgtgatatt gctgaagagc ttggcggcga atgggctgac   2760
cgcttcctcg tgctttacgg tatcgccgct cccgattcgc agcgcatcgc cttctatcgc   2820
cttcttgacg agttcttctg agcgggactc tggggttcga aatgaccgac caagcgacgc   2880
ccaacctgcc atcacgagat ttcgattcca ccgccgcctt ctatgaaagg ttgggcttcg   2940
gaatcgtttt ccgggacgcc ggctggatga tcctccagcg cggggatctc atgctggagt   3000
tcttcgccca ccctaggggg aggctaactg aaacacggaa ggagacaata ccggaaggaa   3060
cccgcgctat gacggcaata aaaagacaga ataaaacgca cggtgttggg tcgtttgttc   3120
ataaacgcgg ggttcggtcc cagggctggc actctgtcga taccccaccg agaccccatt   3180
ggggccaata cgcccgcgtt tcttcctttt ccccacccca ccccccaagt tcgggtgaag   3240
gcccagggct cgcagccaac gtcggggcgg caggccctgc catagcctca ggttactcat   3300
atatacttta gattgattta aaacttcatt tttaatttaa aaggatctag gtgaagatcc   3360
tttttgataa tctcatgacc aaaatccctt aacgtgagtt ttcgttccac tgagcgtcag   3420
accccgtaga aaagatcaaa ggatcttctt gagatccttt ttttctgcgc gtaatctgct   3480
gcttgcaaac aaaaaaacca ccgctaccag cggtggtttg tttgccggat caagagctac   3540
caactctttt tccgaaggta actggcttca gcagagcgca gataccaaat actgtccttc   3600
tagtgtagcc gtagttaggc caccacttca agaactctgt agcaccgcct acatacctcg   3660
ctctgctaat cctgttacca gtggctgctg ccagtggcga taagtcgtgt cttaccgggt   3720
tggactcaag acgatagtta ccggataagg cgcagcggtc gggctgaacg gggggttcgt   3780
gcacacagcc cagcttggag cgaacgacct acaccgaact gagataccta cagcgtgagc   3840
tatgagaaag cgccacgctt cccgaaggga gaaaggcgga caggtatccg gtaagcggca   3900
gggtcggaac aggagagcgc acgagggagc ttccaggggg aaacgcctgg tatctttata   3960
gtcctgtcgg gtttcgccac ctctgacttg agcgtcgatt tttgtgatgc tcgtcagggg   4020
ggcggagcct atggaaaaac gccagcaacg cggccttttt acggttcctg gccttttgct   4080
```

ggccttttgc tcacatgttc tttcctgcgt tatcccctga ttctgtggat aaccgtatta 4140
ccgccatgca t 4151

<210> SEQ ID NO 17
<211> LENGTH: 3429
<212> TYPE: DNA
<213> ORGANISM: human herpesvirus 2
<220> FEATURE:
<221> NAME/KEY: misc_feature
<223> OTHER INFORMATION: Herpes simplex virus type 2 (HSV-2) ribonucleotide reductase (ICP10, RR1) wild-type gene

<400> SEQUENCE: 17
atggccaacc gccctgccgc atccgccctc gccggagcgc ggtctccgtc cgaacgacag 60
gaaccccggg agcccgaggt cgcccccccct ggcggcgacc acgtgttttg caggaaagtc 120
agcggcgtga tggtgctttc cagcgatccc cccggccccg cggcctaccg cattagcgac 180
agcagctttg ttcaatgcgg ctccaactgc agtatgataa tcgacggaga cgtggcgcgc 240
ggtcatttgc gtgacctcga gggcgctacg tccaccggcg ccttcgtcgc gatctcaaac 300
gtcgcagccg gcggggatgg ccgaaccgcc gtcgtggcgc tcggcggaac ctcgggcccg 360
tccgcgacta catccgtggg gacccagacg tccggggagt tcctccacgg gaacccaagg 420
acccccgaac cccaaggacc ccaggctgtc cccccgcccc ctcctccccc ctttccatgg 480
ggccacgagt gctgcgcccg tcgcgatgcc aggggcggcg ccgagaagga cgtcggggcc 540
gcggagtcat ggtcagacgg cccgtcgtcc gactccgaaa cggaggactc ggactcctcg 600
gacgaggata cgggttcgga gacgctgtct cgatcctctt cgatctgggc cgcaggggcg 660
actgacgacg atgacagcga ctccgactcg cggtcggacg actccgtgca gcccgacgtt 720
gtcgttcgtc gcagatggag cgacggcccc gcccccgtgg cctttcccaa gccccggcgc 780
cccggcgact cccccggaaa ccccggcctg ggcgccggca ccgggccggg ctccgcgacg 840
gacccgcgcg cgtcggccga ctccgattcc gcggcccacg ccgccgcacc ccaggcggac 900
gtggcgccgg ttctggacag ccagcccact gtgggaacgg accccggcta cccagtcccc 960
ctagaactca cgcccgagaa cgcggaggcg gtggcgcggt ttctggggga cgccgtcgac 1020
cgcgagcccg cgctcatgct ggagtacttc tgtcggtgcg cccgcgagga gagcaagcgc 1080
gtgcccccac gaaccttcgg cagcgccccc cgcctcacgg aggacgactt tgggctcctg 1140
aactacgcgc tcgctgagat gcgacgcctg tgcctggacc ttcccccggt cccccccaac 1200
gcatacacgc cctatcatct gagggagtat gcgacgcggc tggttaacgg gttcaaaccc 1260
ctggtgcggc ggtccgcccg cctgtatcgc atcctggggg ttctggtcca cctgcgcatc 1320
cgtacccggg aggcctcctt tgaggaatgg atgcgctcca aggaggtgga cctggacttc 1380
gggctgacgg aaaggcttcg cgaacacgag gcccagctaa tgatcctggc ccaggccctg 1440
aacccctacg actgtctgat ccacagcacc ccgaacacgc tcgtcgagcg ggggctgcag 1500
tcggcgctga agtacgaaga gttttacctc aagcgcttcg gcgggcacta catggagtcc 1560
gtcttccaga tgtacacccg catcgccggg tttctggcgt gccgggcgac ccgcggcatg 1620
cgccacatcg ccctggggcg acaggggtcg tggtgggaaa tgttcaagtt ctttttccac 1680
cgcctctacg accaccagat cgtgccgtcc acccccgcca tgctgaacct cggaacccgc 1740
aactactaca cgtccagctg ctacctggta aacccccagg ccaccactaa ccaggccacc 1800
ctccgggcca tcaccggcaa cgtgagcgcc atcctcgccc gcaacggggg catcgggctg 1860
tgcatgcagg cgttcaacga cgccagcccc ggcaccgcca gcatcatgcc ggccctgaag 1920

```
gtcctcgact ccctggtggc ggcgcacaac aaacagagca cgcgccccac cggggcgtgc   1980

gtgtacctgg aaccctggca cagcgacgtt cgggccgtgc tcagaatgaa gggcgtcctc   2040

gccggcgagg aggcccagcg ctgcgacaac atcttcagcg ccctctggat gccggacctg   2100

ttcttcaagc gcctgatccg ccacctcgac ggcgagaaaa acgtcacctg gtccctgttc   2160

gaccgggaca ccagcatgtc gctcgccgac tttcacggcg aggagttcga gaagctgtac   2220

gagcacctcg aggccatggg gttcggcgaa acgatcccca tccaggacct ggcgtacgcc   2280

atcgtgcgca gcgcggccac caccggaagc cccttcatca tgtttaagga cgcggtaaac   2340

cgccactaca tctacgacac gcaaggggcg gccatcgccg gctccaacct ctgcaccgag   2400

atcgtccacc cggcctccaa gcgatccagt ggggtctgca acctgggaag cgtgaatctg   2460

gcccgatgcg tctccaggca gacgtttgac tttgggcggc tccgcgacgc cgtgcaggcg   2520

tgcgtgctga tggtgaacat catgatcgac agcacgctac aacccacgcc ccagtgcacc   2580

cgcggcaacg acaacctgcg gtccatgggc attggcatgc agggcctgca cacggcgtgc   2640

ctcaagatgg gcctggatct ggagtcggcc gagttccggg acctgaacac acacatcgcc   2700

gaggtgatgc tgctcgcggc catgaagacc agtaacgcgc tgtgcgttcg cggggcgcgt   2760

cccttcagcc actttaagcg cagcatgtac cgggccggcc gctttcactg ggagcgcttt   2820

tcgaacgcca gcccgcggta cgagggcgag tgggagatgc tacgccagag catgatgaaa   2880

cacggcctgc gcaacagcca gttcatcgcg ctcatgccca ccgccgcctc ggcccagatc   2940

tcggacgtca gcgagggctt tgccccccctg ttcaccaacc tgttcagcaa ggtgaccagg   3000

gacggcgaga cgctgcgccc caacacgctc ttgctgaagg aactcgagcg cacgttcggc   3060

gggaagcggc tcctggacgc gatggacggg ctcgaggcca agcagtggtc tgtggcccag   3120

gccctgcctt gcctggaccc cgcccacccc ctccggcggt tcaagacggc cttcgactac   3180

gaccaggaac tgctgatcga cctgtgtgca gaccgcgccc cctatgttga tcacagccaa   3240

tccatgactc tgtatgtcac agagaaggcg gacgggacgc tccccgcctc caccctggtc   3300

cgccttctcg tccacgcata taagcgcggc ctgaagacgg ggatgtacta ctgcaaggtt   3360

cgcaaggcga ccaacagcgg ggtgttcgcc ggcgacgaca acatcgtctg cacaagctgc   3420

gcgctgtaa                                                           3429
```

<210> SEQ ID NO 18
<211> LENGTH: 2961
<212> TYPE: DNA
<213> ORGANISM: Artificial Sequence
<220> FEATURE:
<223> OTHER INFORMATION: Description of Artificial Sequence:modified Herpes simplex virus type 2 (HSV-2) ribonucleotide reductase (ICP10, RR1) gene with some amino-terminal serine/threonine protein kinase (PK) domain deleted

<400> SEQUENCE: 18

```
atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420
```

-continued

```
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagagc    720
ggccgcttaa ttaaccacac gccctatcat ctgagggagt atgcgacgcg gctggttaac    780
gggttcaaac ccctggtgcg gcggtccgcc cgcctgtatc gcatcctggg ggttctggtc    840
cacctgcgca tccgtacccg ggaggcctcc tttgaggaat ggatgcgctc caaggaggtg    900
gacctggact tcgggctgac ggaaaggctt cgcgaacacg aggcccagct aatgatcctg    960
gcccaggccc tgaaccccta cgactgtctg atccacagca ccccgaacac gctcgtcgag   1020
cgggggctgc agtcggcgct gaagtacgaa gagttttacc tcaagcgctt cggcgggcac   1080
tacatggagt ccgtcttcca gatgtacacc cgcatcgccg ggtttctggc gtgccgggcg   1140
acccgcggca tgcgccacat cgccctgggg cgacaggggt cgtggtggga aatgttcaag   1200
ttcttttttcc accgcctcta cgaccaccag atcgtgccgt ccacccccgc catgctgaac   1260
ctcggaaccc gcaactacta cacgtccagc tgctacctgg taaaccccca ggccaccact   1320
aaccaggcca ccctccgggc catcaccggc aacgtgagcg ccatcctcgc ccgcaacggg   1380
ggcatcgggc tgtgcatgca ggcgttcaac gacgccagcc ccggcaccgc cagcatcatg   1440
ccggccctga aggtcctcga ctccctggtg gcggcgcaca acaaacagag cacgcgcccc   1500
accggggcgt gcgtgtacct ggaaccctgg cacagcgacg ttcgggccgt gctcagaatg   1560
aagggcgtcc tcgccggcga ggaggcccag cgctgcgaca acatcttcag cgccctctgg   1620
atgccggacc tgttcttcaa gcgcctgatc cgccacctcg acggcgagaa aaacgtcacc   1680
tggtccctgt tcgaccggga caccagcatg tcgctcgccg actttcacgg cgaggagttc   1740
gagaagctgt acgagcacct cgaggccatg gggttcggcg aaacgatccc catccaggac   1800
ctggcgtacg ccatcgtgcg cagcgcggcc accaccggaa gcccctcat catgtttaag    1860
gacgcggtaa accgccacta catctacgac acgcaagggg cggccatcgc cggctccaac   1920
ctctgcaccg agatcgtcca cccggcctcc aagcgatcca gtggggtctg caacctggga   1980
agcgtgaatc tggcccgatg cgtctccagg cagacgtttg actttgggcg gctccgcgac   2040
gccgtgcagg cgtgcgtgct gatggtgaac atcatgatcg acagcacgct acaacccacg   2100
ccccagtgca cccgcggcaa cgacaacctg cggtccatgg gcattggcat gcagggcctg   2160
cacacggcgt gcctcaagat gggcctggat ctggagtcgg ccgagttccg ggacctgaac   2220
acacacatcg ccgaggtgat gctgctcgcg gccatgaaga ccagtaacgc gctgtgcgtt   2280
cgcggggcgc gtcccttcag ccactttaag cgcagcatgt accgggccgg ccgctttcac   2340
tgggagcgct tttcgaacgc cagcccgcgg tacgagggcg agtgggagat gctacgccag   2400
agcatgatga aacacggcct gcgcaacagc cagttcatcg cgctcatgcc caccgccgcc   2460
tcggcccaga tctcggacgt cagcgagggc tttgcccccc tgttcaccaa cctgttcagc   2520
aaggtgacca gggacggcga gacgctgcgc cccaacacgc tcttgctgaa ggaactcgag   2580
cgcacgttcg gcgggaagcg gctcctggac gcgatggacg ggctcgaggc caagcagtgg   2640
tctgtggccc aggccctgcc ttgcctggac cccgcccacc ccctccggcg gttcaagacg   2700
gccttcgact acgaccagga actgctgatc gacctgtgtg cagaccgcgc cccctatgtt   2760
```

-continued gatcacagcc aatccatgac tctgtatgtc acagagaagg cggacgggac gctccccgcc 2820
tccaccctgg tccgccttct cgtccacgca tataagcgcg gcctgaagac ggggatgtac 2880
tactgcaagg ttcgcaaggc gaccaacagc ggggtgttcg ccggcgacga caacatcgtc 2940
tgcacaagct gcgcgctgta a 2961

<210> SEQ ID NO 19
<211> LENGTH: 2247
<212> TYPE: DNA
<213> ORGANISM: Artificial Sequence
<220> FEATURE:
<223> OTHER INFORMATION: Description of Artificial Sequence:modified Herpes simplex virus type 2 (HSV-2) ribonucleotide reductase (ICP10, RR1) gene with amino-terminal serine/threonine protein kinase (PK) domain deleted

<400> SEQUENCE: 19
atgagcggcc gcttaattaa ccacacgccc tatcatctga gggagtatgc gacgcggctg 60
gttaacgggt tcaaacccct ggtgcggcgg tccgcccgcc tgtatcgcat cctgggggtt 120
ctggtccacc tgcgcatccg tacccgggag gcctcctttg aggaatggat gcgctccaag 180
gaggtggacc tggacttcgg gctgacggaa aggcttcgcg aacacgaggc ccagctaatg 240
atcctggccc aggccctgaa cccctacgac tgtctgatcc acagcacccc gaacacgctc 300
gtcgagcggg ggctgcagtc ggcgctgaag tacgaagagt tttacctcaa gcgcttcggc 360
gggcactaca tggagtccgt cttccagatg tacacccgca tcgccgggtt tctggcgtgc 420
cgggcgaccc gcggcatgcg ccacatcgcc ctggggcgac aggggtcgtg gtgggaaatg 480
ttcaagttct ttttccaccg cctctacgac caccagatcg tgccgtccac ccccgccatg 540
ctgaacctcg gaacccgcaa ctactacacg tccagctgct acctggtaaa cccccaggcc 600
accactaacc aggccaccct ccgggccatc accggcaacg tgagcgccat cctcgcccgc 660
aacgggggca tcgggctgtg catgcaggcg ttcaacgacg ccagccccgg caccgccagc 720
atcatgccgg ccctgaaggt cctcgactcc ctggtggcgg cgcacaacaa acagagcacg 780
cgccccaccg ggcgtgcgt gtacctggaa ccctggcaca gcgacgttcg ggccgtgctc 840
agaatgaagg gcgtcctcgc cggcgaggag gcccagcgct gcgacaacat cttcagcgcc 900
ctctggatgc cggacctgtt cttcaagcgc ctgatccgcc acctcgacgg cgagaaaaac 960
gtcacctggt ccctgttcga ccgggacacc agcatgtcgc tcgccgactt tcacggcgag 1020
gagttcgaga agctgtacga gcacctcgag gccatggggt tcggcgaaac gatccccatc 1080
caggacctgg cgtacgccat cgtgcgcagc gcggccacca ccggaagccc cttcatcatg 1140
tttaaggacg cggtaaaccg ccactacatc tacgacacgc aaggggcggc catcgccggc 1200
tccaacctct gcaccgagat cgtccacccg gcctccaagc gatccagtgg ggtctgcaac 1260
ctgggaagcg tgaatctggc ccgatgcgtc tccaggcaga cgtttgactt tgggcggctc 1320
cgcgacgccg tgcaggcgtg cgtgctgatg gtgaacatca tgatcgacag cacgctacaa 1380
cccacgcccc agtgcacccg cggcaacgac aacctgcggt ccatgggcat tggcatgcag 1440
ggcctgcaca cggcgtgcct caagatgggc ctggatctgg agtcggccga gttccgggac 1500
ctgaacacac acatcgccga ggtgatgctg ctcgcggcca tgaagaccag taacgcgctg 1560
tgcgttcgcg gggcgcgtcc cttcagccac tttaagcgca gcatgtaccg ggccggccgc 1620
tttcactggg agcgcttttc gaacgccagc ccgcggtacg agggcgagtg ggagatgcta 1680
cgccagagca tgatgaaaca cggcctgcgc aacagccagt tcatcgcgct catgcccacc 1740

-continued

```
gccgcctcgg cccagatctc ggacgtcagc gagggctttg ccccccctgtt caccaacctg   1800

ttcagcaagg tgaccaggga cggcgagacg ctgcgcccca acacgctctt gctgaaggaa   1860

ctcgagcgca cgttcggcgg gaagcggctc ctggacgcga tggacgggct cgaggccaag   1920

cagtggtctg tggcccaggc cctgccttgc ctggaccccg cccacccct ccggcggttc   1980

aagacggcct tcgactacga ccaggaactg ctgatcgacc tgtgtgcaga ccgcgccccc   2040

tatgttgatc acagccaatc catgactctg tatgtcacag agaaggcgga cgggacgctc   2100

cccgcctcca ccctggtccg ccttctcgtc cacgcatata agcgcggcct gaagacgggg   2160

atgtactact gcaaggttcg caaggcgacc aacagcgggg tgttcgccgg cgacgacaac   2220

atcgtctgca caagctgcgc gctgtaa                                        2247


<210> SEQ ID NO 20
<211> LENGTH: 655
<212> TYPE: DNA
<213> ORGANISM: Artificial Sequence
<220> FEATURE:
<223> OTHER INFORMATION: Description of Artificial Sequence:immediate
      early cytomegalovirus (CMV) constitutive promoter regulatory
      sequence

<400> SEQUENCE: 20

cgatgtacgg gccagatata cgcgttgaca ttgattattg actagttatt aatagtaatc     60

aattacgggg tcattagttc atagcccata tatggagttc cgcgttacat aacttacggt    120

aaatggcccg cctggctgac cgcccaacga cccccgccca ttgacgtcaa taatgacgta    180

tgttcccata gtaacgccaa tagggacttt ccattgacgt caatgggtgg actatttacg    240

gtaaactgcc cacttggcag tacatcaagt gtatcatatg ccaagtacgc cccctattga    300

cgtcaatgac ggtaaatggc ccgcctggca ttatgcccag tacatgacct tatgggactt    360

tcctacttgg cagtacatct acgtattagt catcgctatt accatggtga tgcggttttg    420

gcagtacatc aatgggcgtg gatagcggtt tgactcacgg ggatttccaa gtctccaccc    480

cattgacgtc aatgggagtt tgttttggca ccaaaatcaa cgggactttc caaaatgtcg    540

taacaactcc gccccattga cgcaaatggg cggtaggcgt gtacggtggg aggtctatat    600

aagcagagct ctctggctaa ctagagaacc cactgcttac tggcttatcg aaatt         655
```